US012614637B2

(12) United States Patent
Sabidó Aguade et al.

(10) Patent No.: US 12,614,637 B2
(45) Date of Patent: Apr. 28, 2026

(54) IN VITRO METHOD FOR PREDICTING MORTALITY RISK IN PATIENTS SUFFERING FROM SHOCK

(71) Applicants: FUNDACIÓ INSTITUT D'INVESTIGACIÓ EN CIÈNCIES DE LA SALUT GERMANS TRIAS I PUJOL, Badalona (ES); FUNDACIÓ CENTRE DE REGULACIÓ GENÒMICA, Barcelona (ES); UNIVERSITAT POMPEU FABRA, Barcelona (ES)

(72) Inventors: Eduard Sabidó Aguade, Barcelona (ES); Eva Borràs Ramirez, Barcelona (ES); Ferran Rueda Sobella, Badalona (ES); Antonio Bayés Genis, Badalona (ES); Oriol Iborra Egea, Badalona (ES); Cosme García García, Badalona (ES)

(73) Assignees: FUNDACIÓ INSTITUT D'INVESTIGACIÓ EN CIÈNCIES DE LA SALUT GERMANS TRIAS I PUJOL, Badalona (ES); FUNDACIÓ CENTRE DE REGULACIÓ GENÒMICA, Barcelona (ES); UNIVERSITAT POMPEU FABRA, Barcelona (ES)

( * ) Notice: Subject to any disclaimer, the term of this patent is extended or adjusted under 35 U.S.C. 154(b) by 1261 days.

(21) Appl. No.: 17/432,038

(22) PCT Filed: Feb. 20, 2020

(86) PCT No.: PCT/EP2020/054516
§ 371 (c)(1),
(2) Date: May 16, 2022

(87) PCT Pub. No.: WO2020/169751
PCT Pub. Date: Aug. 27, 2020

(65) Prior Publication Data
US 2024/0290495 A1 Aug. 29, 2024

(30) Foreign Application Priority Data
Feb. 20, 2019 (EP) .................................... 19382126

(51) Int. Cl.
*G01N 33/53* (2006.01)
*G01N 33/68* (2006.01)
*G16H 50/30* (2018.01)

(52) U.S. Cl.
CPC ......... *G16H 50/30* (2018.01); *G01N 33/6893* (2013.01)

(58) Field of Classification Search
None
See application file for complete search history.

(56) References Cited

U.S. PATENT DOCUMENTS

| | | |
|---|---|---|
| 10,673,347 B2 | 6/2020 | Andia et al. |
| 11,224,744 B2 | 1/2022 | Andia et al. |
| 2014/0187519 A1 | 7/2014 | Cooke et al. |
| 2020/0113462 A1 | 4/2020 | Martínez Piñeiro et al. |
| 2020/0354467 A1 | 11/2020 | Sarrias Fornés et al. |
| 2021/0189423 A1 | 6/2021 | Matilla Dueñas et al. |
| 2021/0278405 A1 | 9/2021 | Izquierdo García et al. |

FOREIGN PATENT DOCUMENTS

| | | |
|---|---|---|
| WO | 2017/060525 A1 | 4/2017 |
| WO | 2018/141840 A1 | 8/2018 |

OTHER PUBLICATIONS

Huttenhain et al., Reproducible quantification of cancer-associated proteins in body fluids using targeted proteomics, Sci Transl Med, Jul. 11, 2012, 4(142), pp. 1-25. (Year: 2012).*

Torzewski et al., Animal Models of C-Reactive Protein, Hindawl Publishing Corporation, Mediators of Inflammation, vol. 2014, Article ID 683598, 2014, pp. 1-7. (Year: 2014).*

Van Der Vekiens et al., Human and equine cardiovascular endocrinology: beware to compare, Cardiovascular Endocrinology 2013, vol. 2, No. 4, pp. 67-76. (Year: 2013).*

Bjerrum et al., Measurement of beta-2-microglobulin in serum and plasma by an enzyme-linked immunosorbent assay (ELISA) Clinica Chimica Acta, 155, 1986, pp. 69-76. (Year: 1986).*

Prentice et al., Novel proteins associated with risk for coronary heart disease or stroke among postmenopausal women identified by in-depth plasma proteome profiling, Genome Medicine, 2010, 2:48, pp. 1-13. (Year: 2010).*

Xiaoyi et al., "Mortality Predicting Value of Increased Beta2-Microglobulin Level in Acute Myocardial Infarction," *Geriatrics and Health Care* 23(6):481-484, Dec. 25, 2017 (Includes English Abstract). (4 pages).

Borras et al., "Protein-Based Classifier to Predict Conversion from Clinically Isolated Syndrome to Multiple Sclerosis," *The American Society for Biochemistry and Molecular Biology, Inc*:318-328, 2016.

Harola et al., "Clinical picture and risk prediction of short-term mortality in cardiogenic shock," *European Journal of Heart Failure* 17:501-509, 2015.

(Continued)

*Primary Examiner* — Gary Counts
(74) *Attorney, Agent, or Firm* — Seed Intellectual Property Law Group LLP

(57) ABSTRACT

In vitro method for predicting mortality risk in patients suffering from shock. The present invention refers to the medical field. Particularly, it refers to an in vitro method for predicting mortality risk among patients suffering from shock, which comprises determining in a biological sample obtained from the patient the concentration level of specific proteins.

15 Claims, 20 Drawing Sheets

Specification includes a Sequence Listing.

(56)                    References Cited

OTHER PUBLICATIONS

Iborra-Egea et al., "Molecular signature of cardiogenic shock," *European Heart Journal* 0:1-12, 2019.

Nemoto et al., "Experimental Evaluation of the Influence of Complete Artificial Circulation on Renal Circulation and Tissue Metabolism-Comparative Study of Pulsatile vs Nonpulsatile Circulation-," *Ann Thorac Cardiovasc Surg* 9(6):355-364, 2003.

O'Gara et al., "2013 ACCF/AHA Guideline for the Management of ST-Elevation Myocardial Infarction: A Report of the American College of Cardiology Foundation/American Heart Association Task Force on Practice Guidelines," *Journal of American College of Cardiology* 61(4), 2013. (63 pages).

Rueda et al., "Protein-based cardiogenic shock patient classifier," *European Heart Journal* 40:2684-2694, 2019.

Singer et al., "The Third International Consensus Definitions for Sepsis and Septic Shock (Sepsis-3)," *JAMA* 315(8):801-810, 2016.

Steg et al., "ESC Guidelines for the management of acute myocardial infarction in patients presenting with ST-segment elevation," *European Heart Journal* 33:2569-2619, 2012.

Tolppanen et al., "Adrenomedullin: a marker of impaired hemodynamics, organ dysfunction, and poor prognosis in cardiogenic shock," *Annals of Intensive Care* 7(6), 2017. (10 pages).

Wang et al., "The prognostic values of beta-2 microglobulin for risks of cardiovascular events and mortality in the elderly patients with isolated systolic hypertension," *Journal of Research in Medical Sciences* 23(82), 2018. (8 pages).

\* cited by examiner

CS4P

Survivors   Non-Survivors

Patient Classification

4-Protein Biomarker Panel 0.83 AUC

VALIDATION

Protein 1

Protein 2

Protein 3

Protein 4

Targeted Quantification

CardShock Patient Cohort

51 Protein Candidates

DISCOVERY

Mass Spectrometry

Barcelona Patient Cohort

2662 Quantified Proteins

SEQUENCE LISTING

```
<160> NUMBER OF SEQ ID NOS: 6

<210> SEQ ID NO 1
<211> LENGTH: 10
<212> TYPE: PRT
<213> ORGANISM: ARTIFICIAL SEQUENCE
<220> FEATURE:
<223> OTHER INFORMATION: sequence used for obtaining the mass
      spectrometry chromatographic profile of the protein

<400> SEQUENCE: 1

Val Glu His Ser Asp Leu Ser Phe Ser Lys
1               5                   10

<210> SEQ ID NO 2
<211> LENGTH: 22
<212> TYPE: PRT
<213> ORGANISM: ARTIFICIAL SEQUENCE
<220> FEATURE:
<223> OTHER INFORMATION: sequence used for obtaining the mass
      spectrometry chromatographic profile of the protein

<400> SEQUENCE: 2

Ser Asn Phe Leu Asn Cys Tyr Val Ser Gly Phe His Pro Ser Asp Ile
1               5                   10                  15

Glu Val Asp Leu Leu Lys
            20

<210> SEQ ID NO 3
<211> LENGTH: 13
<212> TYPE: PRT
<213> ORGANISM: ARTIFICIAL SEQUENCE
<220> FEATURE:
<223> OTHER INFORMATION: sequence used for obtaining the mass
      spectrometry chromatographic profile of the protein

<400> SEQUENCE: 3

Leu Asp Gln Gly Gly Ala Pro Leu Ala Gly Thr Asn Lys
1               5                   10
```

```
<210> SEQ ID NO 4
<211> LENGTH: 13
<212> TYPE: PRT
<213> ORGANISM: ARTIFICIAL SEQUENCE
<220> FEATURE:
<223> OTHER INFORMATION: sequence used for obtaining the mass
      spectrometry chromatographic profile of the protein

<400> SEQUENCE: 4

Glu Thr Thr Ile Gln Gly Leu Asp Gly Leu Ser Glu Arg
1               5                   10

<210> SEQ ID NO 5
<211> LENGTH: 8
<212> TYPE: PRT
<213> ORGANISM: ARTIFICIAL SEQUENCE
<220> FEATURE:
<223> OTHER INFORMATION: sequence used for obtaining the mass
      spectrometry chromatographic profile of the protein

<400> SEQUENCE: 5

Phe Thr Ile Thr Ala Gly Ser Lys
1               5

<210> SEQ ID NO 6
<211> LENGTH: 12
<212> TYPE: PRT
<213> ORGANISM: ARTIFICIAL SEQUENCE
<220> FEATURE:
<223> OTHER INFORMATION: sequence used for obtaining the mass
      spectrometry chromatographic profile of the protein

<400> SEQUENCE: 6

Leu Val Leu Leu Asn Ala Ile Tyr Leu Ser Ala Lys
1               5                   10
```

IN VITRO METHOD FOR PREDICTING MORTALITY RISK IN PATIENTS SUFFERING FROM SHOCK

STATEMENT REGARDING SEQUENCE LISTING

The Sequence Listing associated with this application is provided in text format in lieu of a paper copy, and is hereby incorporated by reference into the specification. The name of the text file containing the Sequence Listing is 370099_401USPC_SEQUENCE_LISTING.txt. The text file is 2.3 KB, was created on Apr. 8, 2022, and is being submitted electronically via EFS-Web.

FIELD OF THE INVENTION

The present invention refers to the medical field. Particularly, it refers to an in vitro method for predicting mortality risk among patients suffering from shock, which comprises determining in a biological sample obtained from the patient the concentration level of specific proteins.

STATE OF THE ART

Despite the generalization of early revascularization and modern intensive care, shock management, particularly cardiogenic shock (CS), remains challenging, with mortality rates of ~40%. Early and accurate risk stratification is crucial for prompt identification of the sickest patients who may benefit from advanced therapies. While clinical predictors of adverse outcome have been well-known for decades, their derivation from pre-PCI (Percutaneous Coronary Intervention) clinical trials and a lack of external validation precluded their routine use and prompted the development of more contemporary risk classifiers. Two scores have been recently reported. The CardShock risk score was developed from a large prospective multicenter European registry of unselected CS patients with a broad spectrum of etiologies, two-thirds with ST-Elevation Myocardial Infarction (STEMI). The IABP-SHOCK II risk score was developed from IABP-SHOCK II trial participants and is highly specific for PCI-treated STEMI-related CS. These two scores are externally validated and include classical clinical and biochemical variables for short-term risk stratification.

Notably, the laboratory parameters included in these risk scores are basic biochemical tests (glucose and lactate) that have been routinely used in the clinic for several decades, but also include some clinical acumen parameters. More recent studies have explored cardiac and extra-cardiac predictive biomarkers in CS. However, most of these studies are small or not validated by external cohorts or did not assess the incremental predictive value of such biomarkers combined with current clinical practice. Particularly, novel renal biomarkers, including cystatin C, plasma neutrophil gelatinase-associated lipocalin, and kidney injury molecule-1, have not performed better than conventional creatinine. With regards to proteomics data in other cardiovascular pathology contexts, a proteomics approach was recently reported in the setting of stable coronary artery disease, in which a 9-protein risk score was reported with a C-statistic of 0.74.

Thus, well into the 21$^{st}$ century, shock in general, and CS in particular, remain associated with unacceptable high mortality, substantial morbidity and resource utilization. Despite widespread use of early coronary reperfusion, CS occurs with a prevalence of approximately 5% in STEMI and it is the leading cause of in-hospital death.

Therefore, although, as cited above, some contemporary risk scores are available, including the CardShock and IABP-SHOCK II risk scores, more accurate risk stratification strategies are needed in order to efficiently predict mortality risk in shock patients.

On the other hand, accumulating evidence indicates that CS is not only a pump failure problem but is rather a systemic inflammatory status within the context of multiorgan failure. Therefore, comprehensive proteomics may enable the unbiased discovery of novel protein biomarkers that can be used to acquire pathophysiological knowledge, improve risk stratification accuracy, and identify therapeutic targets.

The present invention is actually focused on solving the above cited problem and it is based on a protein-based score to predict short-term mortality risk among patients with shock, particularly CS. Thus, this precise stratification of shock patients (particularly patients suffering from CS), according to their short-term mortality risk, can be effectively used to foresee or anticipate the treatment mainly in those cases with a high mortality risk, increasing the likelihood of success of the treatment and consequently the life expectancy of the patient suffering from shock.

DESCRIPTION OF THE INVENTION

Brief Description of the Invention

In the present invention, a quantitative proteomics analyses in two independent CS cohorts for the discovery and validation of CS biomarkers was performed. Moreover, a cohort for the discovery and validation of septic sock (SS) biomarkers was performed.

Twenty-six proteins listed in Table 1 were initially identified as biomarkers for predicting mortality risk among patients suffering from CS.

Among said twenty-six proteins, the four proteins described below were identified as preferred candidates both in CS and SS, for which the measured levels substantially improved mortality risk prediction beyond established contemporary clinical risk scores:

L-FABP. UniProt reference P07148.
B2MG. UniProt reference P61769.
ALDOB. UniProt reference P05062.
IC1. UniProt reference P05155.

Thus, based on the results, a protein-based classifier was developed, which was also tested by mass spectrometry and ELISA. This classifier accurately discriminates shock patients according to their short-term mortality risk.

Particularly, the inventors have developed an in vitro method for discriminating those patients suffering from shock, or who have suffered from shock, with low mortality risk from those patients suffering from shock, or who have suffered from shock, with high mortality risk. Specifically, a circulating protein-based score has been developed to predict short-term mortality risk among patients with CS or SS. In a particularly preferred embodiment the method is focused on CS and comprises measuring, in combination, the concentration level of four specific proteins (CS4P model) namely: L-FABP, B2MG, ALDOB and IC1. The area under the curve (AUC) for this CS4P model is 0.83 (see FIG. 8). The AUC for CardShock (which is a standard risk score) is 0.78. The combination of both models (CS4P+CardShock) gives rise to an improved AUC of 0.84 (see FIG. 6).

On the other hand, it is important to note that the model based on the combination of the twenty-six proteins listed in Table 1 gives rise to an improved AUC in CS of 0.921 (see FIG. 10) when this model is not combined with CardShock. Moreover, an improved AUC of 0.970 was obtained when the twenty-six proteins listed in Table 1 was also combined with CardShock (see FIG. 9).

Moreover, said twenty-six proteins and, more particularly, said four proteins L-FABP, B2MG, ALDOB and IC1 have been individually analyzed in the present invention (see FIGS. 5, 6, 7 and 8). The levels of L-FABP, B2MG and ALDOB are higher in non-survivors CS patients relative to survivors. Conversely, the level of IC1 is lower in non-survivors CS patients relative to survivors (see FIG. 4).

The proteins of the invention were preferably measured within 24 hours of the patient admission. On the other hand, the method is particularly directed to determine "short-term" mortality risk among CS patients. According to the present invention, "short term" means 90 days. So, in a preferred embodiment, the method of the invention is actually evaluating the mortality risk among shock patients within a period of 90 days.

On the other hand, the method of the invention can be considered as a non-invasive or minimally invasive technique because it is preferably performed in serum or plasma samples obtained from the patients.

Although, in a particularly preferred embodiment, the method of the invention is based on determining the concentration level of the above cited twenty six proteins in combination, preferably the four proteins B2MG, L-FABP, ALDOB and IC1 in combination, it is important to consider that the present invention could be also performed by determining the concentration level of a reduced number of said twenty six proteins or even a reduced number of said four proteins. In other words, the present invention could be implemented by using any of the individual 26 proteins listed above, particularly one, two, three or four of the proteins: B2MG, L-FABP, ALDOB and IC1.

On the other hand, B2MG is herein cited as a preferred individual protein for implementing the invention because, such as it can be observed in Table 2, it offers the best individual results in CS when it is determined by ELISA (method more readily suitable for routine clinical use) without the need of being combined with CardShock. However, the present invention offers scientific support (see FIGS. 5, 6, 7 and 8), for the use of any of the 26 proteins listed in Table 1, preferably any of the following proteins B2MG, L-FABP, ALDOB or IC1 as individual biomarkers, or any combination thereof, for predicting mortality risk among patients suffering from shock, preferably CS or SS. Consequently, the present invention also refers to the use of any of the 26 proteins listed above, or any combination thereof, for predicting mortality risk among patients suffering from shock, preferably CS or SS. In a preferred embodiment said combination of proteins comprises at least 2, at least 3 or at least 4 of the proteins: B2MG, L-FABP, ALDOB or IC1. Thus B2MG or, alternatively, any of the 26 proteins listed above, preferably any of the following proteins: L-FABP, ALDOB or IC1, or any combination thereof, are identified in the present invention as biomarkers suitable for predicting mortality risk among patients suffering from shock, preferably CS or SS. Consequently, the present invention provides evidence for the use of any of the above cited proteins, or any combination thereof, as biomarkers showing a high sensitivity and sensibility, for predicting mortality risk among patients suffering from shock, preferably CS or SS.

So, the first embodiment of the present invention refers to an in vitro method for predicting mortality risk among patients suffering from shock which comprises determining in a biological sample obtained from the patient at least the concentration level of any individual protein listed above, preferably at least B2MG, or of at least L-FABP, or of at least ALDOB, or of at least IC1, wherein an increased level of at least the protein B2MG or of at least L-FABP, or of at least ALDOB, or a reduced level of at least IC1, with respect to the concentration level of said proteins determined in survivor patients suffering from shock, is an indication of mortality risk. In a preferred embodiment, the method of the invention comprises determining the concentration level of the proteins B2MG, L-FABP, ALDOB and IC1, wherein an increased level of the proteins B2MG, L-FABP and ALDOB, and a decreased level of the protein IC1, with respect to the concentration level determined in survivor patients suffering from shock, is an indication of mortality risk. In a preferred embodiment, the method of the invention further comprises performing CardShock. CardShock includes the following variables: Age>75 years, confusion at presentation, previous myocardial infarction or coronary artery bypass grafting (CABG), acute coronary syndrome (ACS) etiology, left ventricular ejection fraction<40%, blood lactate, and eGFR$_{CKD-EPI}$. In a preferred embodiment, the method of the invention is performed within 24 hours from the patient admission. In a preferred embodiment, the mortality risk is evaluated within a period of 90 days. In a preferred embodiment, the biological sample is serum or plasma. In a preferred embodiment, the mortality risk is predicted in the present invention in patients with CS, hypovolemic shock, anaphylactic shock, SS or neurogenic shock, preferably in patients with CS or SS, more preferably in patients with CS. In this sense, please refer to FIGS. 11 to 13, which provide ROC curves showing the AUC for the individual proteins L-FABP, B2MG, ALDOB and IC1, and combinations thereof, for predicting mortality risk in patients with SS.

The second embodiment of the present invention refers to the in vitro use of any of the 26 proteins listed above, preferably at least B2MG, or of at least L-FABP, or of at least ALDOB, or of at least IC1, for predicting mortality risk among patients suffering from shock, preferably CS or SS. In a preferred embodiment, said use comprises determining the concentration level of B2MG, L-FABP, ALDOB and IC1. In a preferred embodiment, said use further comprises performing CardShock. CardShock includes the following variables: Age>75 years, confusion at presentation, previous myocardial infarction or coronary artery bypass grafting (CABG), acute coronary syndrome (ACS) etiology, left ventricular ejection fraction<40%, blood lactate, and eGFR$_{CKD-EPI}$.

When the method of the invention comprises measuring the concentration level of a combinations of biomarkers, a score value is obtained for the signature and this score value is compared with a threshold value which defines the diagnostic rule. If a variation of the score value is identified with respect to the threshold, then the corresponding sample is classified as a positive sample, which is an indication of an increased mortality risk of the patient suffering from CS. The threshold value has been defined in order to optimize sensitivity and specificity values. Consequently, in a preferred embodiment, the method of the invention comprises: a) Measuring the concentration level of any of the above cited combinations of biomarkers, in a biological sample obtained from the subject, b) processing the concentration values in order to obtain a risk score and c) wherein if a deviation or variation of the risk score value obtained for any of the above cited combinations of biomarkers is identified, as compared with a reference value, this is an indication of an increased mortality risk of the patient suffering from CS.

The third embodiment of the present invention refers to a method for treating patients suffering from shock, or patients who have suffered from shock, which comprises treating said patients with a suitable treatment after determining, by means of the method described above, their mortality risk. Thus, this precise stratification of shock patients (particularly patients suffering from CS or SS), according to their short-term mortality risk, can be effectively used to foresee or anticipate the treatment mainly in those cases with a high mortality risk, increasing the likelihood of success of the treatment and consequently the life expectancy of the patient suffering from shock. In a preferred embodiment the patients are suffering or has suffered from CS, hypovolemic shock, anaphylactic shock, SS or neurogenic shock, preferably from CS or septic shock, and more preferably from CS.

In a preferred embodiment the methods of the invention are performed by ELISA or mass spectrometry. In a preferred embodiment, the measurement of the proteins is performed at their precursors (if any), or mid-regional sections.

The fourth embodiment of the present invention refers to a kit adapted for predicting mortality risk among patients suffering from cardiogenic shock which comprises: a) Tools or media for obtaining a serum or plasma sample from the patient, and b) Tools or media for measuring the concentration level of at least B2MG. In a preferred embodiment, the kit comprises: a) Tools or media for obtaining a serum or plasma sample from the patient, and b) Tools or media for measuring the concentration level of B2MG and L-FABP and ALDOB and IC1.

On the other hand, there are established treatment strategies when a patient is suffering from CS. Early revascularization (mainly through percutaneous coronary intervention (PCI)) is the current, most important, treatment strategy in CS after myocardial infarction, with a significant mortality reduction after 6 months, 1 year, and 6 years. In clinical practice revascularization should be limited to the culprit lesion with possible staged revascularization of other lesions at a later timepoint. There may also be a role for emergent coronary artery bypass grafting (CABG) revascularization; however, there is little evidence to guide surgical vs. PCI revascularization. In this regard, antiplatelet and antithrombotic therapy (including but not limited to glycoprotein IIb/IIIa-inhibitors and cangrelor) is one of the key features for PCI success. There are no specific trials in CS for antiplatelets or anticoagulation. Enteral resorption is impaired in CS and oftentimes opioids are co-administered with further impact on enteral bioavailability.

In the intensive care unit, CS treatment involves initial hemodynamic stabilization by volume expansion, vasopressors, and inotropes plus additional therapy for prevention or treatment of multiorgan system dysfunction (MODS). Inotropes and vasopressors are administered in approximately 90% of patients in CS. In case of an abnormal heart rhythm, immediate synchronized cardioversion or anti-arrhythmic agents may be administered, e.g. adenosine. Positive inotropic agents (such as dobutamine or milrinone), which enhance the heart's pumping capabilities, are used to improve the contractility and correct the low blood pressure. CS may also be treated with intravenous dobutamine simultaneously to norepinephrine, which acts on $\beta 1$ receptors of the heart leading to increased contractility and heart rate. Other inotropes such as levosimendan or phosphodiesteraseinhibitors are of interest based on their myocardial contractility improvement and potential for vasodilation without increasing oxygen requirements. However, current evidence for inodilators in CS is very limited. Should that not suffice, the application of mechanical circulatory support is necessary. Intra-aortic balloon pump reduces workload for the heart and improves perfusion of the coronary arteries. Ventricular assist devices (VADs) augment the pump-function of the heart. New developments in VADs include right ventricle support devices such as the Impella RP (Abiomed, Danvers, MA, USA) and the TandemHeart RA-PA (LivaNova, London, UK) with blood delivery from the right atrium or inferior vena cava to the pulmonary artery. Newer left ventricular VADs include the HeartMate PHP (Abbott, Lake Bluff, IL, USA) deployed across the aortic valve and delivering blood from the left ventricle into the aorta similar to the Impella family. Another investigational device is the paracorporeal pulsatile iVAC 2L (PulseCath BV, Arnhem, The Netherlands). Recent developments with miniaturized systems and percutaneous cannula insertion have led to a wider adoption by interventional cardiologists for the treatment of CS using extracorporeal life support systems (ECMO), which have been proposed lately to help CS patients. Integral features of ECMO are the blood pump, a heat exchanger, and an oxygenator. As a general reflection on mechanical circulatory support, the IABP-SHOCK II has shown that a large percentage of CS survivors, could survive without any device. Inserting a device in these patients will have no impact on survival or may even lead to some complications by the device itself possibly resulting in death. Among the 40-50% not surviving, there may also be futile situations where even the best available device will not be able to change clinical outcome. This futile situation may occur in the range of 25-35% for patients with severe CS or those with anoxic brain injury or with concomitant severe sepsis. In these, mechanical circulatory support may be used as a bridge-to-decision strategy and discussion with relatives for a patient-centred decision, but requires a prognostic measurement to validate such decisions, which the field currently lacks. Finally, as a last resort, if the person is stable enough and otherwise qualifies, heart transplantation can be recommended, or, if not eligible for heart transplantation, an artificial heart can be placed. One of the preferred treatment strategies are ventricular assist devices. In this sense, the biomarkers described in the present invention, mainly B2MG, L-FABP, ALDOB and/or IC1, can be used to design companion diagnostic kits or tests to determine the applicability of the above-mentioned treatments to a specific person suffering from CS, for example ventricular assist devices. Consequently, these companion diagnostic kits or tests could help the clinicians in selecting or excluding patient groups for a specific treatment, for example with ventricular assist devices, and to determine responders and non-responders to the therapy. So, by measuring the concentration level of B2MG, L-FABP, ALDOB and/or IC1, the clinicians could predict whether a specific patient would respond to a treatment, for example with ventricular assist device. On the other hand, the clinicians could monitor and follow up the response of a specific patient to the treatment, for example with ventricular assist devices, by measuring the concentration level of B2MG, L-FABP, ALDOB and/or IC1.

For the purpose of the present invention the following terms are defined:

The expression "concentration level determined in control survivor patients suffering from shock", refer to a "reference value" of the concentration level of the proteins. If the concentration levels of L-FABP, B2MG and/or ALDOB are higher, and/or the concentration level of IC1 is lower, as compared with said "concentration level determined in control survivor patients suffering from shock" which is used as a "reference value", this is an indication of mortality risk.

A "reference value" can be a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Preferably, the person skilled in the art may compare the biomarker levels (or scores) obtained according to the method of the invention with a defined threshold value. Typically, the optimal sensitivity and specificity (and so the threshold value) can be determined using a Receiver Operating Characteristic (ROC) curve based on experimental data. For example, after determining the levels of the biomarkers in a group of reference, one can use algorithmic analysis for the statistic treatment of the measured concentrations of biomarkers in biological samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is good. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0.

The term "mortality risk" refers to the estimation of the likelihood of in-hospital death for a patient. According to the present invention, mortality risk exists when the concentration levels of L-FABP, B2MG and/or ALDOB are higher, and/or the concentration level of IC1 is lower, as compared with said "concentration level determined in control survivor patients suffering from shock" which is used as a "reference value".

The term "shock" refers to a life-threatening condition that occurs when the body is not getting enough blood flow. Lack of blood flow means the cells and organs do not get enough oxygen and nutrients to function properly. Many organs can be damaged as a result. Shock requires immediate treatment and can get worse very rapidly. The main types of shock include: Cardiogenic shock (due to heart problems), hypovolemic shock (caused by too little blood volume), anaphylactic shock (caused by allergic reaction), septic shock (due to infections) and neurogenic shock (caused by damage to the nervous system).

By "comprising" it is meant including, but not limited to, whatever follows the word "comprising". Thus, use of the term "comprising" indicates that the listed elements are required or mandatory, but that other elements are optional and may or may not be present.

By "consisting of" it is meant "including, and limited to", whatever follows the phrase "consisting of". Thus, the phrase "consisting of" indicates that the listed elements are required or mandatory, and that no other elements may be present.

DETAILED DESCRIPTION OF THE INVENTION

Example 1. Material and Methods

Example 1.1. Patient Cohorts

Figure 1:
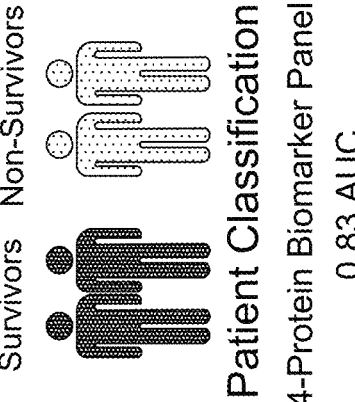
FIG. 1. General workflow of this study in CS patients.
Figure 1:
Figure 1:
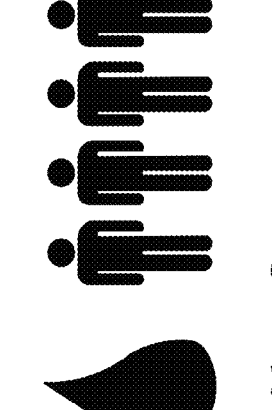

The Barcelona discovery cohort is prospective single-center all-comers study of patients with STEMI-derived CS between March 2011 and March 2015. STEMI was defined according to the Third Universal Definition of Myocardial Infarction. Patient management was determined by the physicians, following guideline recommendations. [Steg P G, James S K, Atar D, et al. *ESC Guidelines for the management of acute myocardial infarction in patients presenting with ST-segment elevation. Eur Heart J* 2012; 33(20): 2569-619] and [O'Gara P T, Kushner F G, Ascheim D D, et al. 2013-2013; 61(4): e78-140].

Two samples were obtained (admission and 24 hours) from every patient (n=48) by venipuncture and stored at −80° C. The clinical end-point was 90-day mortality. The CardShock validation cohort is a European prospective, multicenter, multinational CS study of ischemic or non-ischemic origin between October 2010 and December 2012. Cohort clinical characteristics and inclusion and exclusion criteria are reported elsewhere [Harjola V P, Lassus J, Sionis A, et al; *CardShock Study Investigators; GREAT network. Clinical picture and risk prediction of short-term mortality in cardiogenic shock. Eur J Heart Fail* 2015; 17(5): 501-9].

For the present study, only one sample withdrawn within 24 hours of admission, immediately frozen and stored at −80° C., was used (n=97). During follow-up, vital status was determined by direct contact with the patients or their next of kin, or from population and hospital registers. The clinical end-point was 90-day mortality.

Both cohorts were approved by local ethics committees at the participating centers, and studies were conducted in accordance with the Declaration of Helsinki. Written consent was obtained from the patients or their next of kin.

The septic shock cohort analyzed was composed of 200 patients, provided by the Department of Anesthesiology and Critical Care and Burn Unit, GH St-Louis-Lariboisière, Paris, France.

Serum samples were collected for each patient diagnosed with septic shock, as defined by the Society of Critical Care Medicine (SCCM) and the European Society of Intensive Care Medicine (ESICM), which launched the Surviving Sepsis Campaign Guidelines: Septic shock is defined as a subset of sepsis with circulatory and cellular/metabolic dysfunction associated with higher risk of mortality [Singer M, Deutschman C S, Seymour C W, et al. *The Third International Consensus Definitions for Sepsis and Septic Shock (Sepsis-3). JAMA.* 2016; 315(8):801-810. doi: 10.1001/jama.2016.0287]. Samples were stored at −80° C. and sent to Barcelona for further analysis. During follow-up, vital status was determined by direct contact with the patients or their next of kin, or from population and hospital registers. Out of 200 patients, 104 (52%) survived and 96 (48%) deceased during the follow up. The clinical end-point was 90-day mortality. This cohort was approved by local ethics committees at the participating centers, and studies were conducted in accordance with the Declaration of Helsinki. Written consent was obtained from the patients or their next of kin.

Example 1.2. Biomarker Discovery by Screening Proteomic

Quantitative proteomics analysis was performed using mass spectrometry (nLC-MS/MS) to identify potential protein biomarker candidates among those proteins differing in abundance between 90-day survivors and non-survivors. Serum samples (admission and 24 hours) from 48 patients of the Barcelona cohort (21 non-survivors and 27 survivors at 90 days) were trypsin digested to peptides and analyzed using label-free screening proteomics (nLC-MS/MS).

Example 1.3. Biomarker Validation by Targeted Proteomics

Candidate biomarker proteins identified in the discovery phase, were evaluated in terms of classification power in the CardShock validation cohort with targeted proteomics quantification using parallel reaction monitoring (PRM). Plasma samples corresponding to 97 patients from the CardShock cohort (36 non-survivors and 61 survivors at 90 days), were trypsin digested and analyzed using targeted nLC-PRM and isotopically-labeled standard peptides as internal references. Fragment ion chromatographic traces for all targeted precursor peptides were evaluated, logarithmic transformed and normalized using the internal reference peptides. Protein abundances were estimated, and protein relative quantification was assessed between survivors and non-survivors.

Example 1.4. Enzyme-Linked Immunosorbent Assays of Validated Proteins

Four commercially available ELISA kits were used, following the instructions of the manufacturer, for each validated protein.

L-FABP was quantitative determined by Human L-FABP ELISA Kit. The minimum concentration which can be measured was 102 pg/mL and the measurable concentration range was 102-25,000 pg/ml. Samples had to be diluted at least 20× before use and they were diluted 1/100 in dilution buffer 1× prior measurement. The method of analysis was according to the supplier's manual. There is not cross-reactivity with human H-FABP and human I-FABP.

ALDOB was measured by an Enzyme-linked Immunosorbent Assay Kit. The standard curve range used was 2.5-160 ng/ml and the minimum detectable concentration was 0.9 ng/ml. Intra-assay and inter assay precision was <10% and <12%, respectively. Samples were diluted 1/8 in Phosphate Buffered Saline (PBS) 1× prior measurement. No significant cross-reactivity or interference between ALDOB and analogues was observed.

B2MG was determined by an Enzyme Immunoassay. The calculation range of this ELISA was 0-12 µg/ml, where the functional sensitivity was determined in 0.1 µg/ml. Intra-assay and inter assay precision was <3.5% and <4.5%, respectively. Samples were diluted 1/100 in sample buffer PU 1× prior measurement. No interference has been observed with haemolytic (up to 1000 mg/dl) or lipemic (up to 3 g/dl) serum. The analysis was performed according to the manual.

Serpin G1 was measured by the Human SERPING1 ELISA. The sensitivity or the minimum detectable dose was 10 pg/mL and the detection range was 156-10,000 pg/mL. Intra-assay and inter assay precision were <5.6% and <5.9%, respectively. Samples were diluted 1/50,000 in sample diluent prior measurement. This assay has high specificity for natural and recombinant human SerpinG1 and there is no detectable cross-reactivity with other relevant proteins.

Example 1.5. Statistical Analyses

Clinical variables are presented as number (n) and percentage (%) for categorical variables, mean and standard deviation (SD) for normally distributed variables, or median and interquartile range (IQR) for skewed variables. Comparisons between groups were performed using the chi-square test, Student's t-test, or Mann-Whitney U-test as appropriate.

Protein abundance estimates and relative protein quantification between groups (survivors vs. non-survivors) from proteomics data were performed with the software packages Skyline 3.7 and MSstats 3.8.2. The best protein combinations for classifying 90-day mortality risk in patients with CS were challenged within the CardShock cohort, who was divided into training (⅔) and a validation set (⅓). Within the training set the abundance of each protein was fitted in a logistic regression model between survivors and non-survivors, and the classification ability of each protein and protein combinations was evaluated by the area under the curve (AUC) of a receiver operating characteristic (ROC) curve as previously described. The four identified proteins were tested as continuous variables.

The CardShock risk score, used as baseline model, includes age>75 years, confusion at presentation, previous myocardial infarction or coronary artery bypass grafting (CABG), acute coronary syndrome (ACS) etiology, left ventricular ejection fraction<40%, blood lactate, and eGFR$_{CKD-EPI}$. Model calibrations were calculated using the Hosmer-Lemeshow (HL) test, and patient discrimination and reclassification were evaluated using the Harrell C-statistic (AUC) and continuous net reclassification improvement (cNRI). Confidence intervals for the C-statistic and the NRI were obtained by 1000-fold bootstrap resampling.

Analyses were performed using STATA V.13.0 (StataCorp, College Station, TX), PredictABEL R package v1.2, and SPSS V.20.0 (IBM Corp, Armonk, NY).

Example 2. Results

Example 2.1. Unbiased Discovery of Protein Biomarker Candidates (Barcelona Cohort)

Table 3 shows the clinical, biochemical, and follow-up data from the Barcelona discovery cohort. The mean age was 69±13 years, 35% were women, and 94% were treated with primary percutaneous coronary intervention. 90-day mortality was 45.8%.

A total of 2662 proteins were identified in the dataset, of which 488 were present in over 30% of the patients. After protein relative quantification among the different variables: patient outcome (survivors, non-survivors), and sampling time (admission, 24 hours), a total of 51 proteins were selected for the validation phase in the independent CardShock cohort. Briefly, 32 proteins that changed in abundance either between survivor and non-survivor patients or within the first 24 hours after admission (admission, 24 h) were considered for further validation. Additionally, 19 proteins were included in the study based on previous knowledge and clinical relevance.

Example 2.2. Targeted Proteomics Validation of Circulating Biomarker Candidates (CardShock Cohort)

The classification power of 26 of the 51 selected proteins was further validated in the CardShock cohort using targeted proteomics quantification by parallel reaction monitoring. Table 3 shows the characteristics of the CardShock validation cohort. The mean age was 66±14 years, 25% were women, and 90-day mortality was 37.1%. The most common cause of CS was ACS (71%), mainly driven by STEMI (52%). Compared to the Barcelona Cohort, CardShock patients exhibited higher hemoglobin and lower creatinine, lactate, and glucose levels.

Figure 2A:
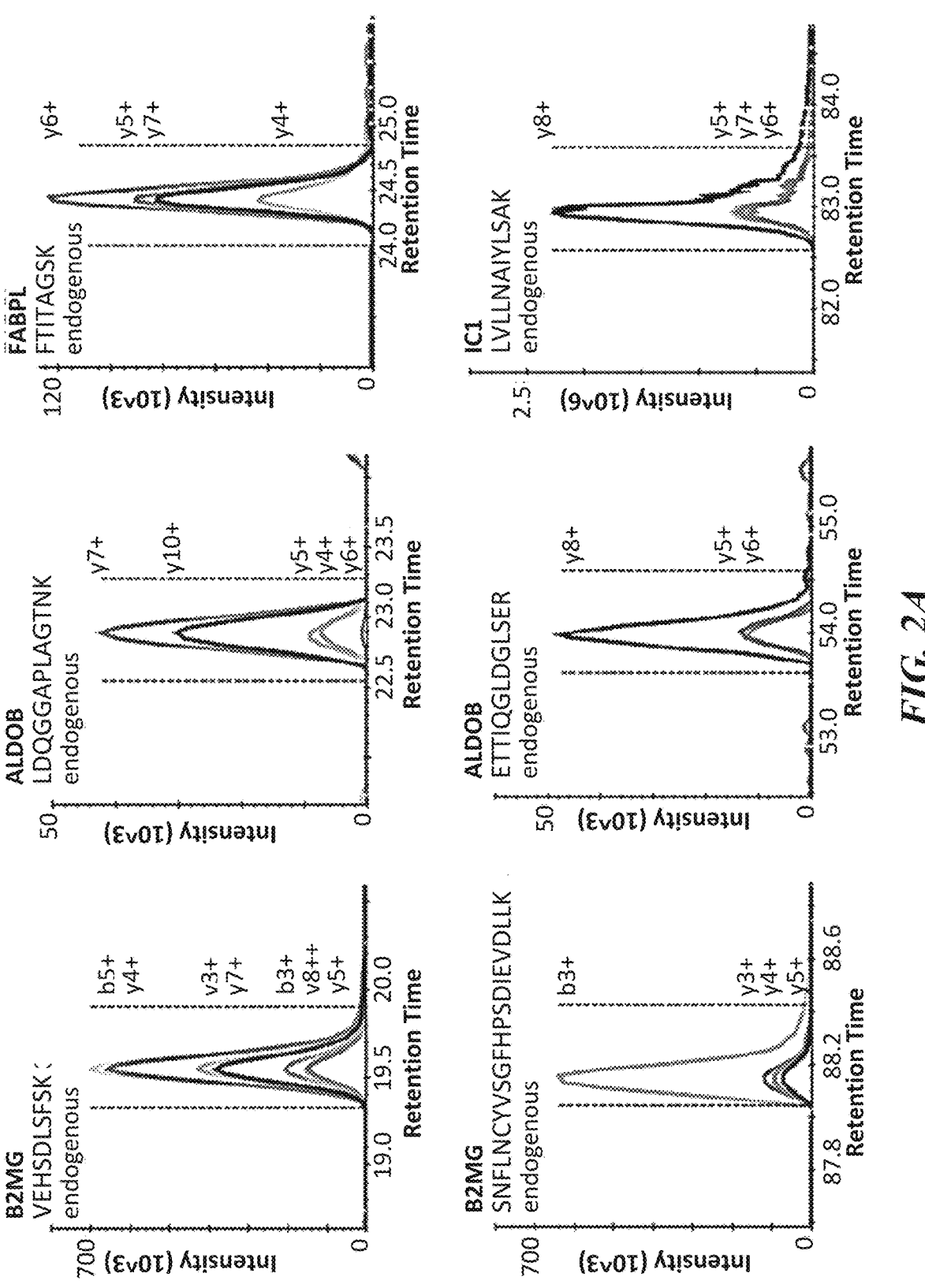
FIG. 2. Targeted proteomics results in CS patients. A) Targeted mass spectrometry chromatographic profiles (PRM) corresponding to the endogenous peptides and their isotopically-labeled internal standards (or reference MS2 spectra) of the proteins L-FABP, B2MG, ALDOB, and IC1. B) Retention time drift of the endogenous peptides shown in panel A for all analyzed patients. L-FABP, Liver-type fatty acid-binding protein; ALDOB, Fructose-bisphosphate aldolase B; B2MG, Beta-2-microglobulin; IC1, SerpinG1.
Figure 2B:
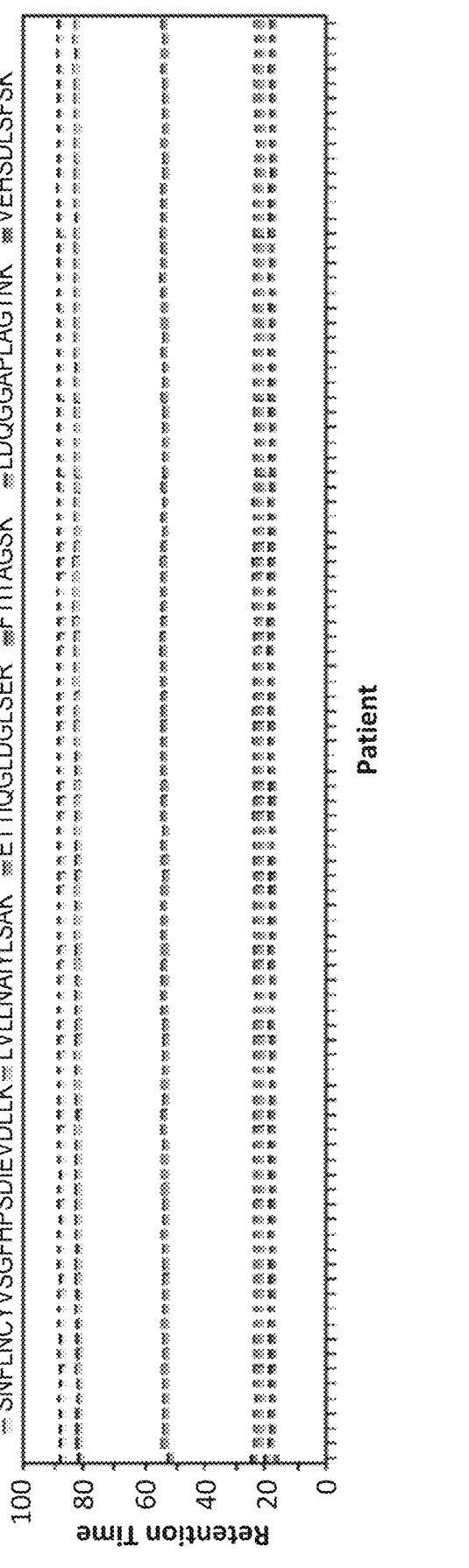

Targeted mass spectrometry chromatographic profiles were obtained for all measured proteins and compared to the corresponding internal references for relative protein quantification. See FIG. 2 as an example for the obtained mass spectrometric signals for proteins Liver-type fatty acid-binding protein (L-FABP), the Fructose-bisphosphate aldolase B (ALDOB), the Beta-2-microglobulin (B2MG), and the SerpinG1 (IC1), measured in all patients. The best protein combinations for classifying 90-day survivors and non-survivors in CS patients were identified by performing a predictor selection combined with cross-validation as previously described [Borras E, Canto E, Choi M, et al. *Protein-Based Classifier to Predict Conversion from Clinically Isolated Syndrome to Multiple Sclerosis. Mol Cell Proteomics.* 2016; 15(1): 318-28]. According to the FIG. 2, the following sequences were used for obtaining the mass spectrometry chromatographic profile for each protein: SEQ ID NO: 1 and SEQ ID NO: 2 for B2MG, SEQ ID NO: 3 and SEQ ID NO: 4 for ALDOB, SEQ ID NO: 5 for FABPL and SEQ ID NO: 6 for ID1. Please note that although this method has been used in the present invention for the identification of the protein, any other part of the protein, or even the entire protein could be used for this purpose.

Figure 3:
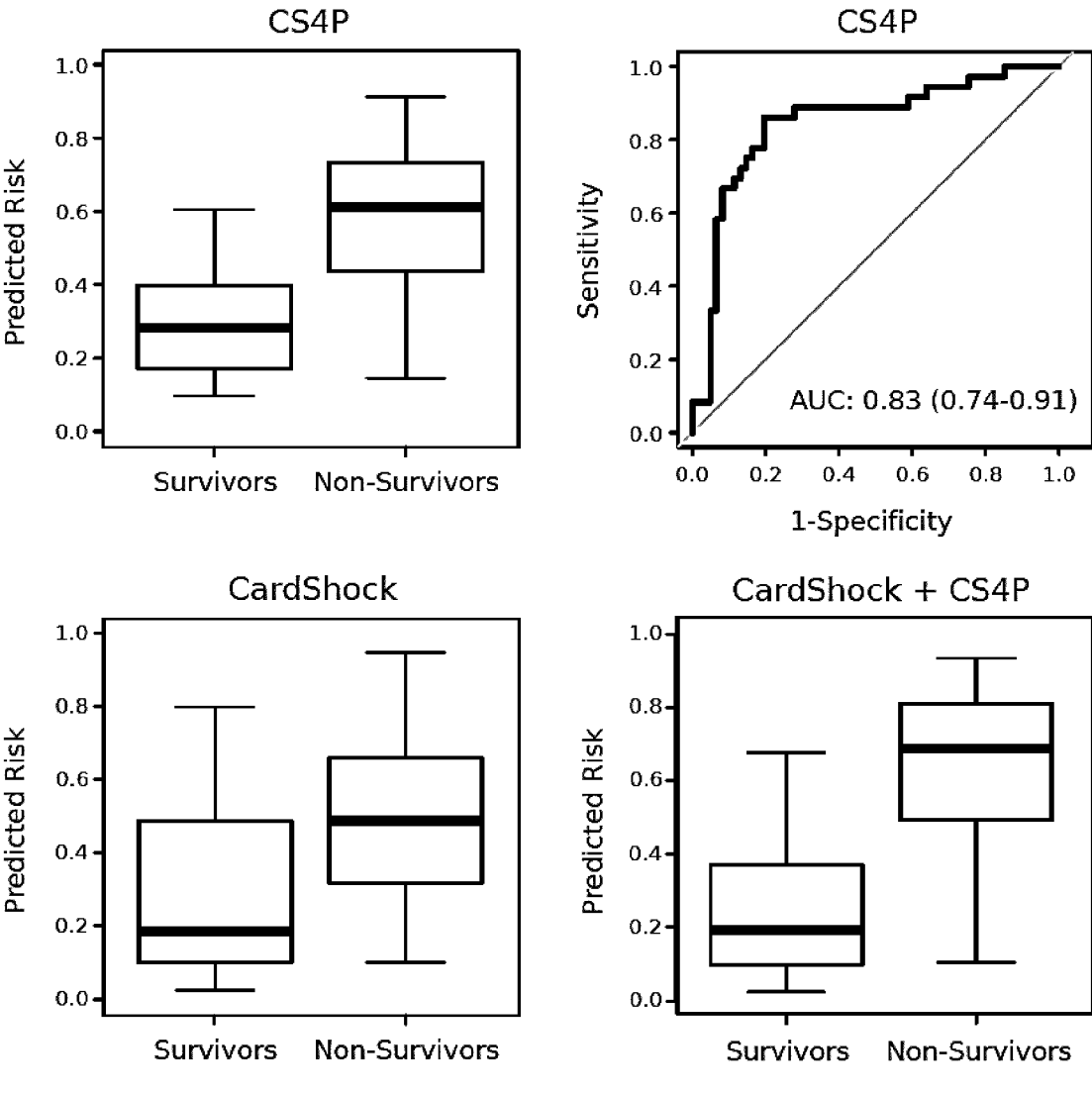
FIG. 3. Improvement in discrimination for prediction of 90-day mortality risk with each model in CS patients. CardShock includes age>75 years, confusion at presentation, previous MI or CABG, ACS etiology, LVEF<40%, blood lactate, and eGFR$_{CKD-EPI}$. CS4P score includes circulating protein abundance measured by parallel reaction monitoring of the Liver-type fatty acid-binding protein (L-FABP), the Fructose-bisphosphate aldolase B (ALDOB), the Beta-2-microglobulin (B2MG), and the SerpinG1 (IC1). CardShock+CS4P include CardShock risk score plus the CS4P score.

This evaluation resulted in the identification of a 4-protein combination with proteins L-FABP, B2MG, ALDOB and IC1 as the best protein classifier to identify short-term mortality risk with an AUC of 0.83 (95% CI 0.74-0.89) (Table 4 and FIG. 3).

An additional model was constructed by combining the CardShock risk score with the new CS4P model (Card-Shock+CS4P). The CardShock+CS4P significantly improved the C-statistics for mortality prediction compared with the CardShock risk score alone (AUC 0.84 vs. AUC 0.78; P=0.033; Table 4 and FIG. 3). Furthermore, the CardShock+CS4P showed a marked benefit in patient reclassification, with an NRI of 0.49 (P=0.020) (Table 4). Overall, CardShock+CS4P resulted in an improved reclassification of 32% of patients compared to CardShock risk score.

In an exploratory analysis, we also combined the CS4P model with another contemporary risk score, the IABP-SHOCK II, generating the IABP-SHOCK II+CS4P. The IABP-SHOCK II+CS4P also provided better prediction metrics compared to IABP-SHOCK II, with an NRI of 0.57 (P=0.032).

Figure 4:
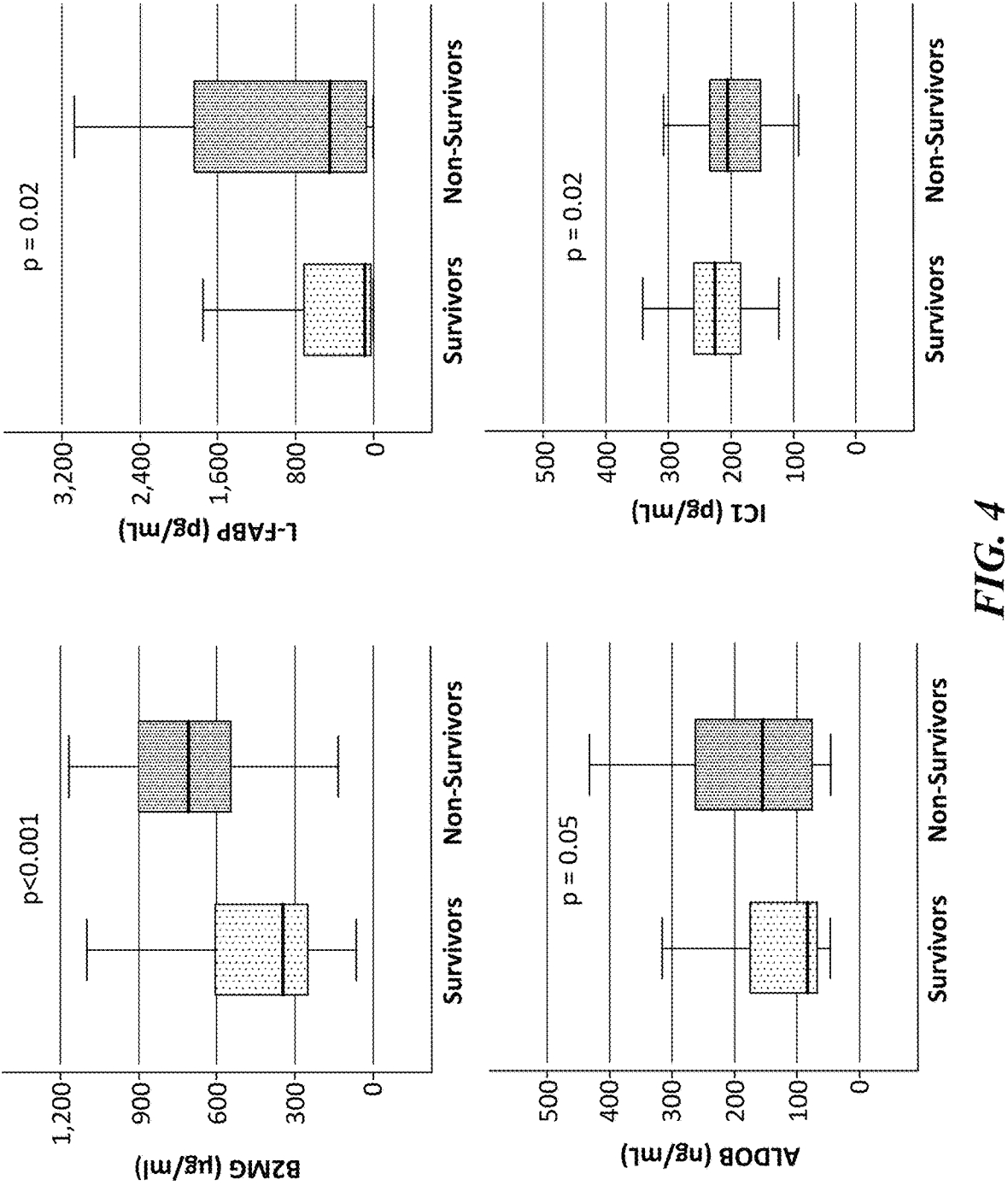
FIG. 4. Box-plots relative to 90-day survivors vs. non-survivors of the 4 proteins of the CS4P measured by ELISA in CS patients. L-FABP, Liver-type fatty acid-binding protein; ALDOB, Fructose-bisphosphate aldolase B; B2MG, Beta-2-microglobulin; IC1, SerpinG1.
Figure 5:
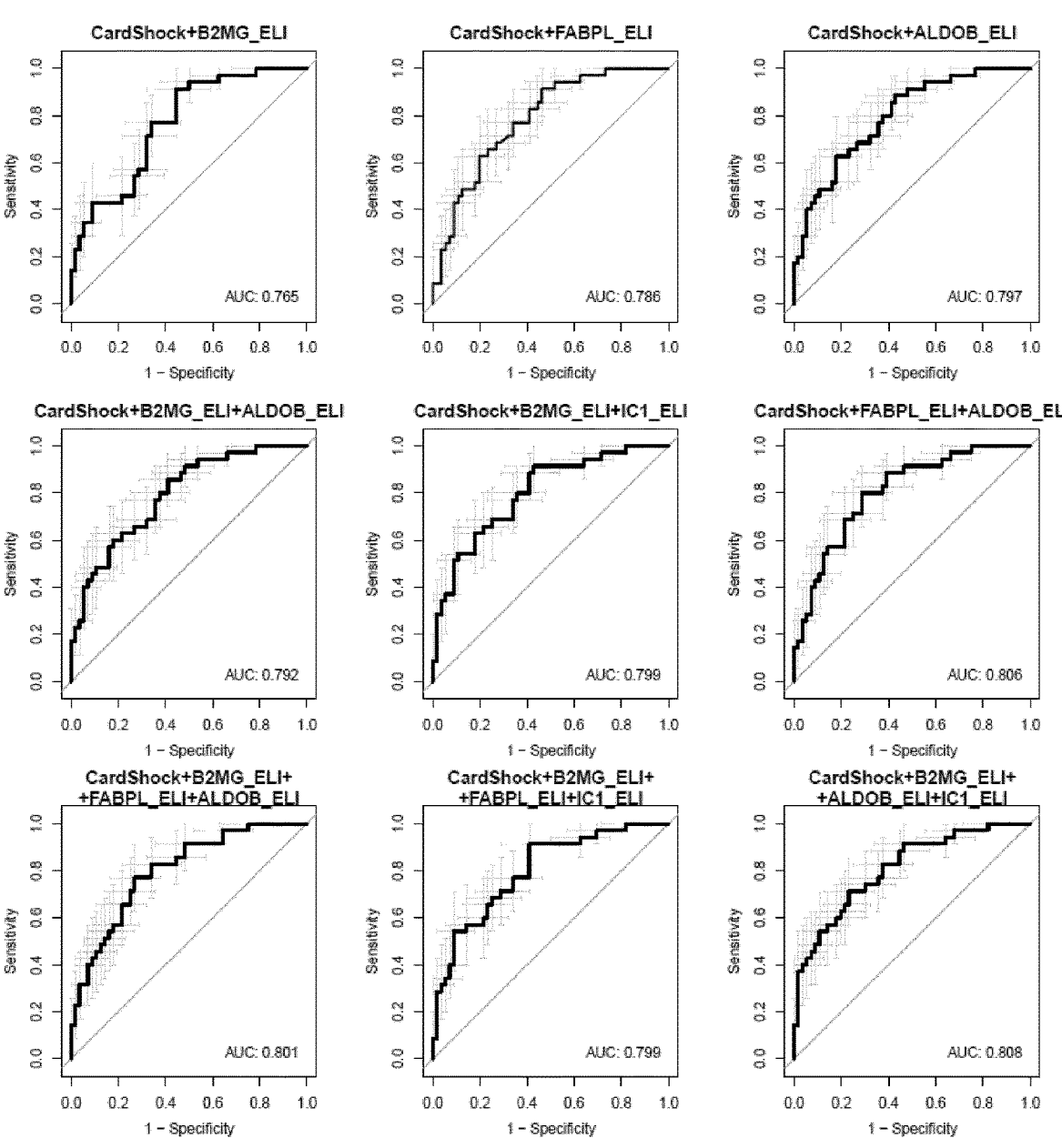
FIG. 5. ROC curves showing the AUC for the individual proteins L-FABP, B2MG, ALDOB and IC1, and combinations thereof, for predicting mortality risk among patients suffering from CS, when said proteins are combined with CardShock and are measured by ELISA.
Figure 5:
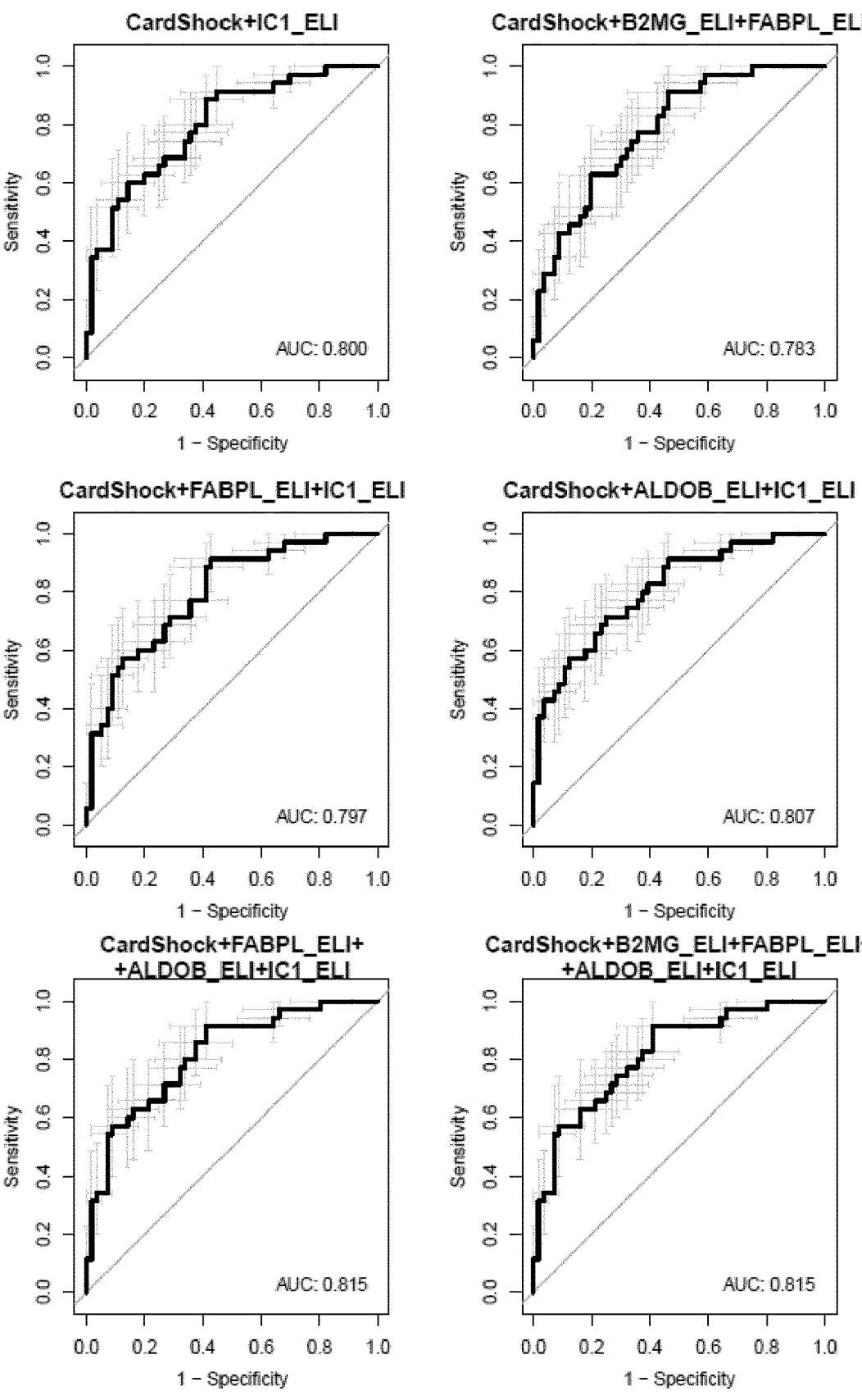
Figure 6:
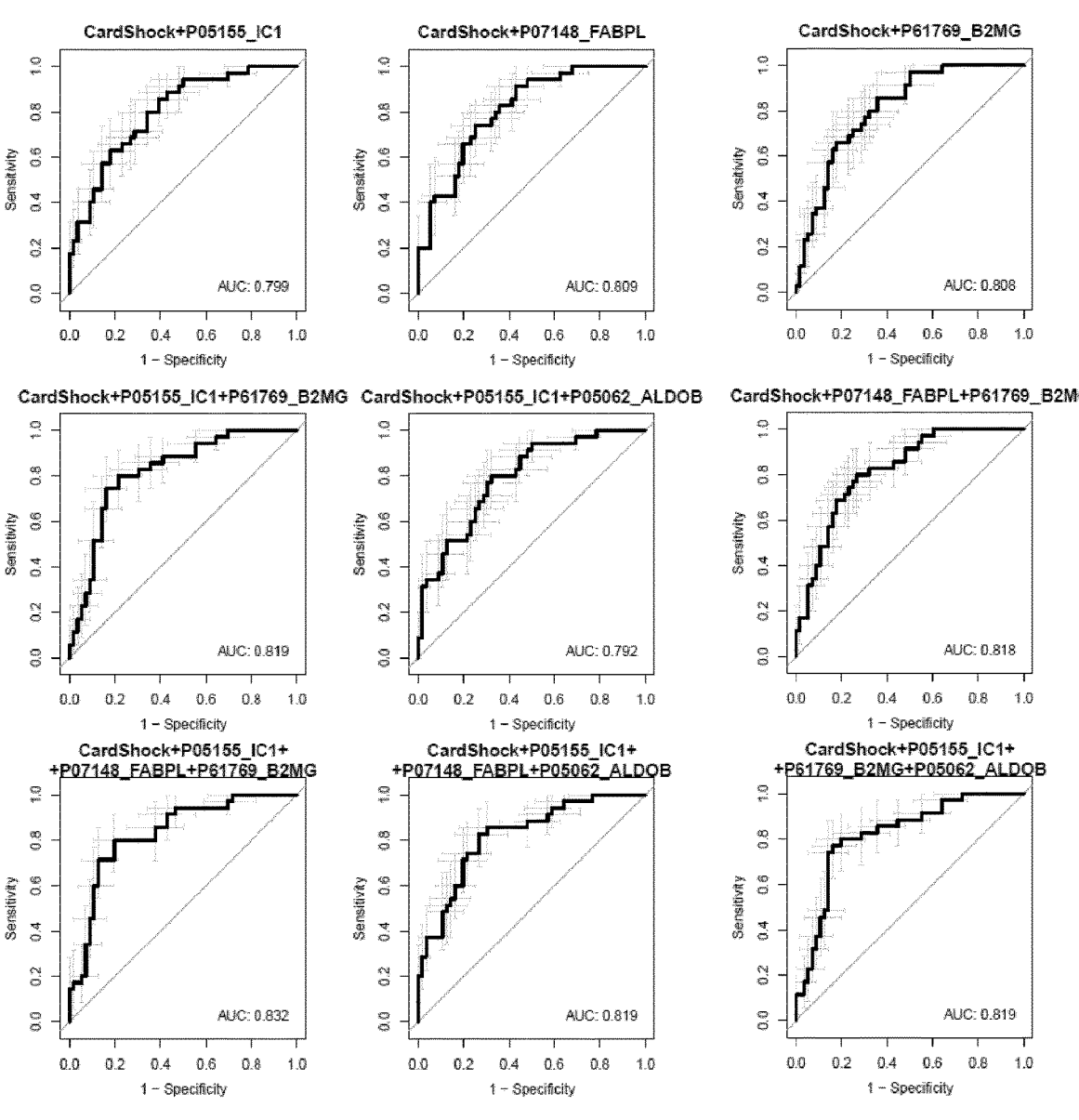
FIG. 6. ROC curves showing the AUC for the individual proteins L-FABP, B2MG, ALDOB and IC1, and combinations thereof, for predicting mortality risk among patients suffering from CS, when said proteins are combined with CardShock and are measured by mass spectrometry.
Figure 6:
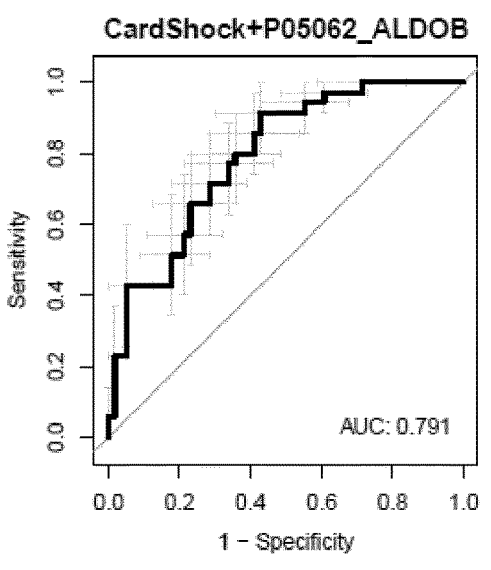
Figure 6:
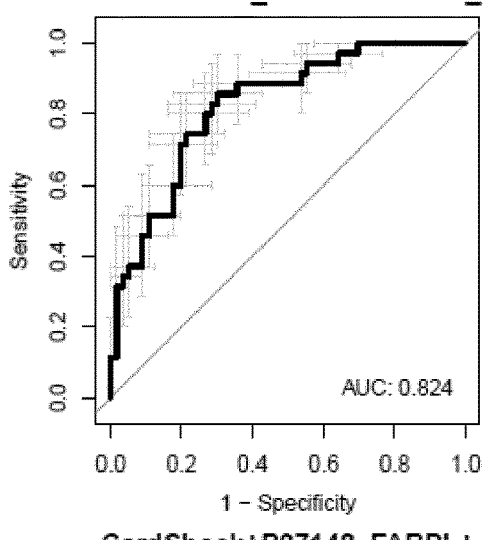
Figure 6:
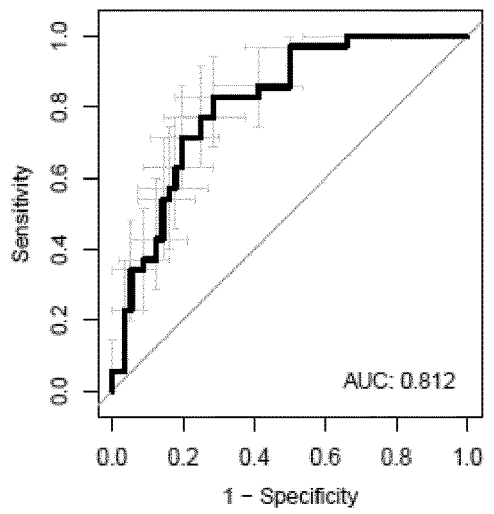
Figure 6:
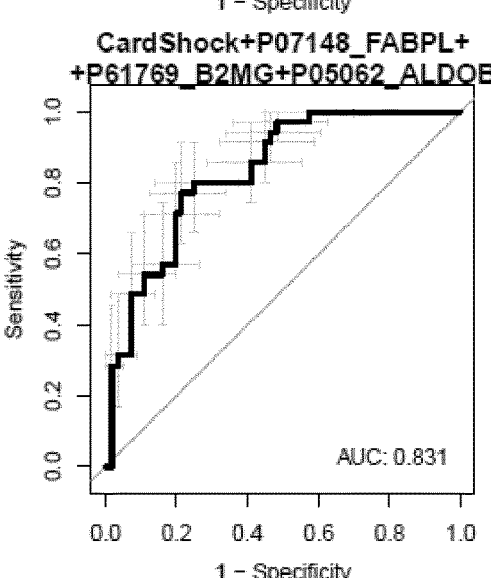
Figure 6:
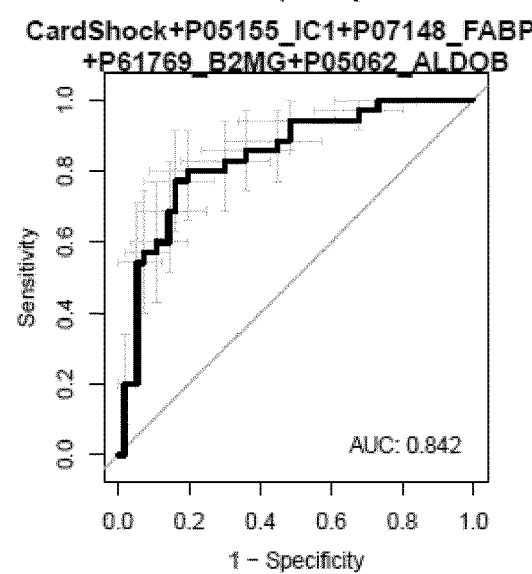
Figure 7:
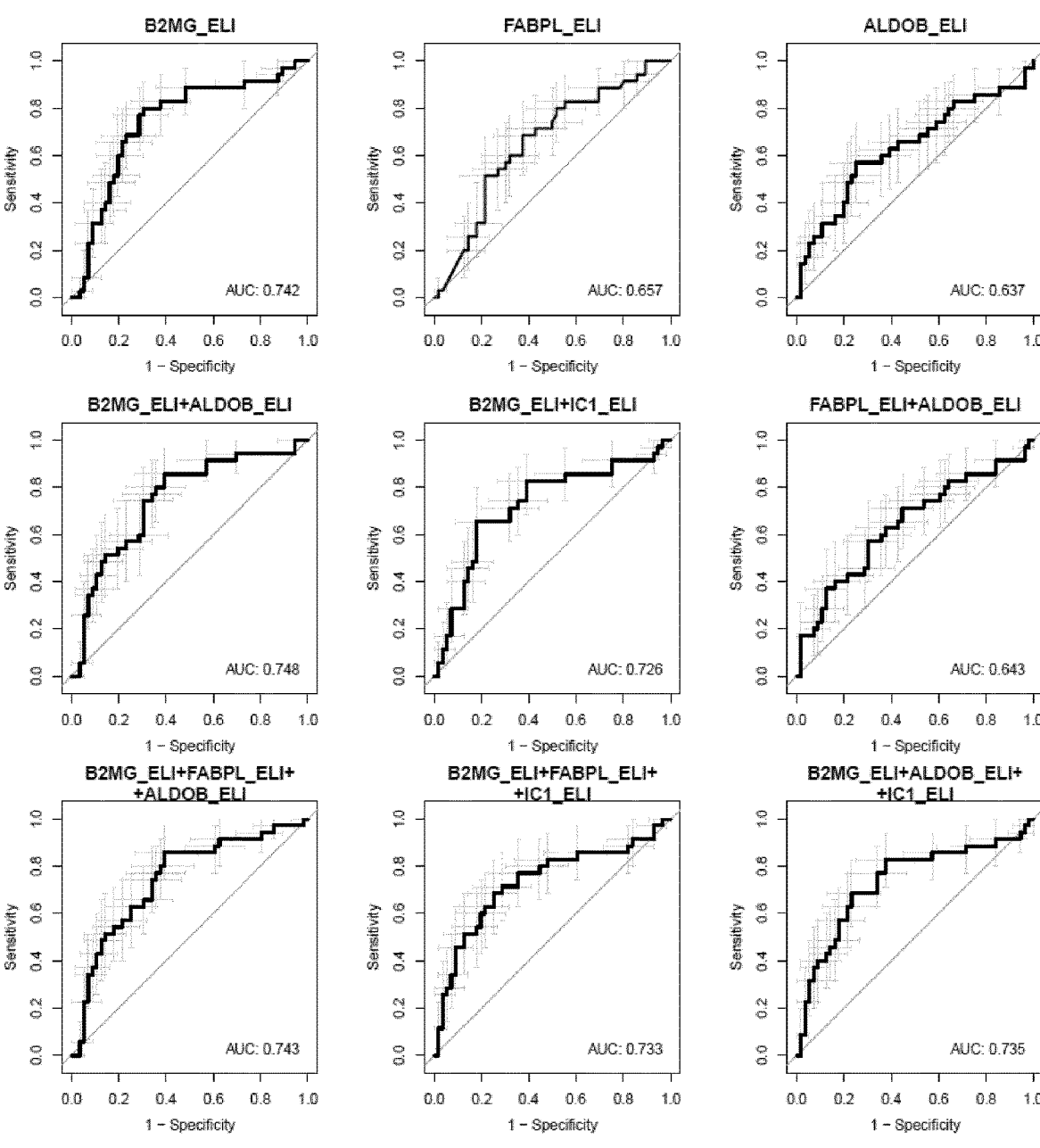
FIG. 7. ROC curves showing the AUC for the individual proteins L-FABP, B2MG, ALDOB and IC1, and combinations thereof, for predicting mortality risk among patients suffering from CS, when said proteins are not combined with CardShock and are measured by ELISA.
Figure 7:
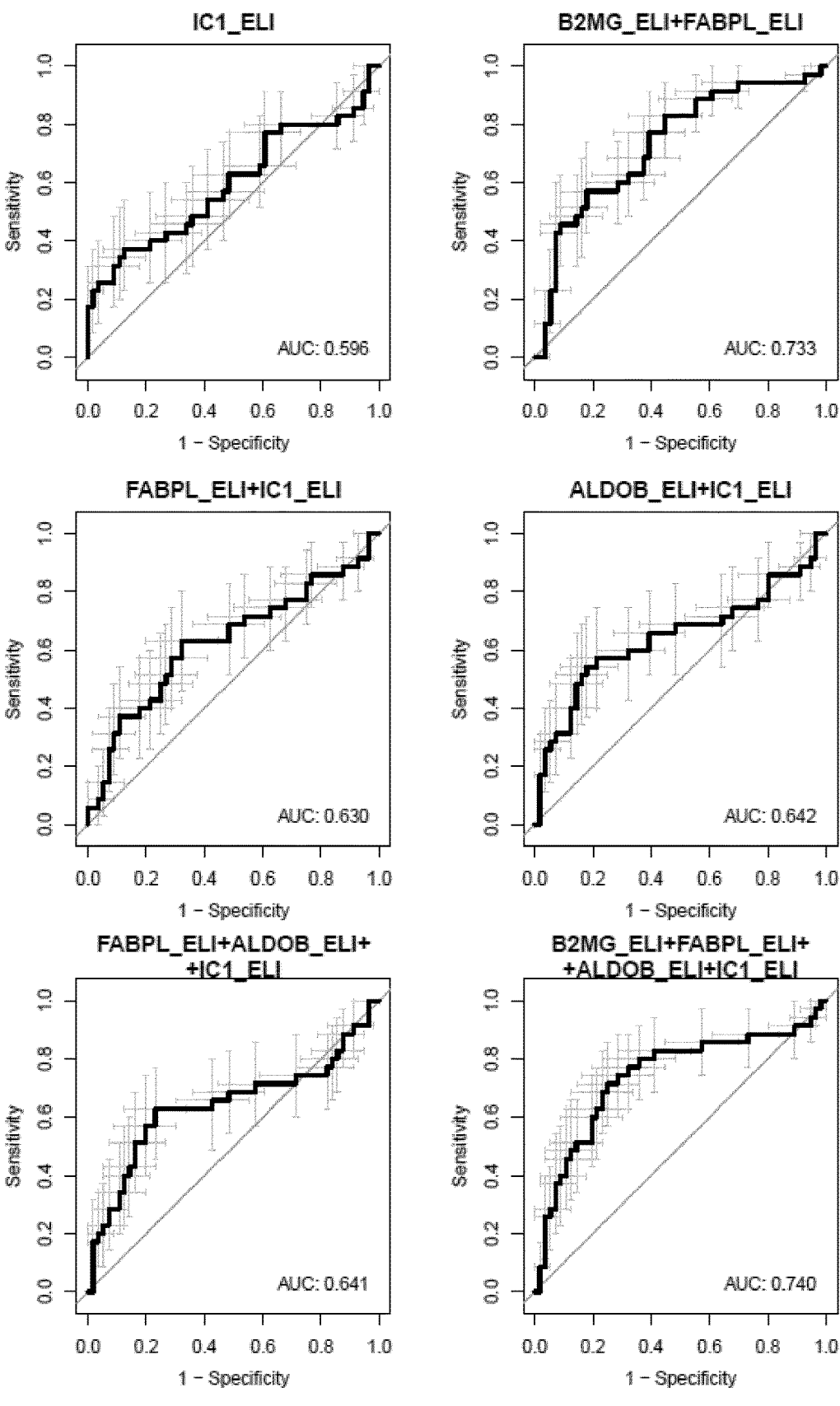
Figure 8:
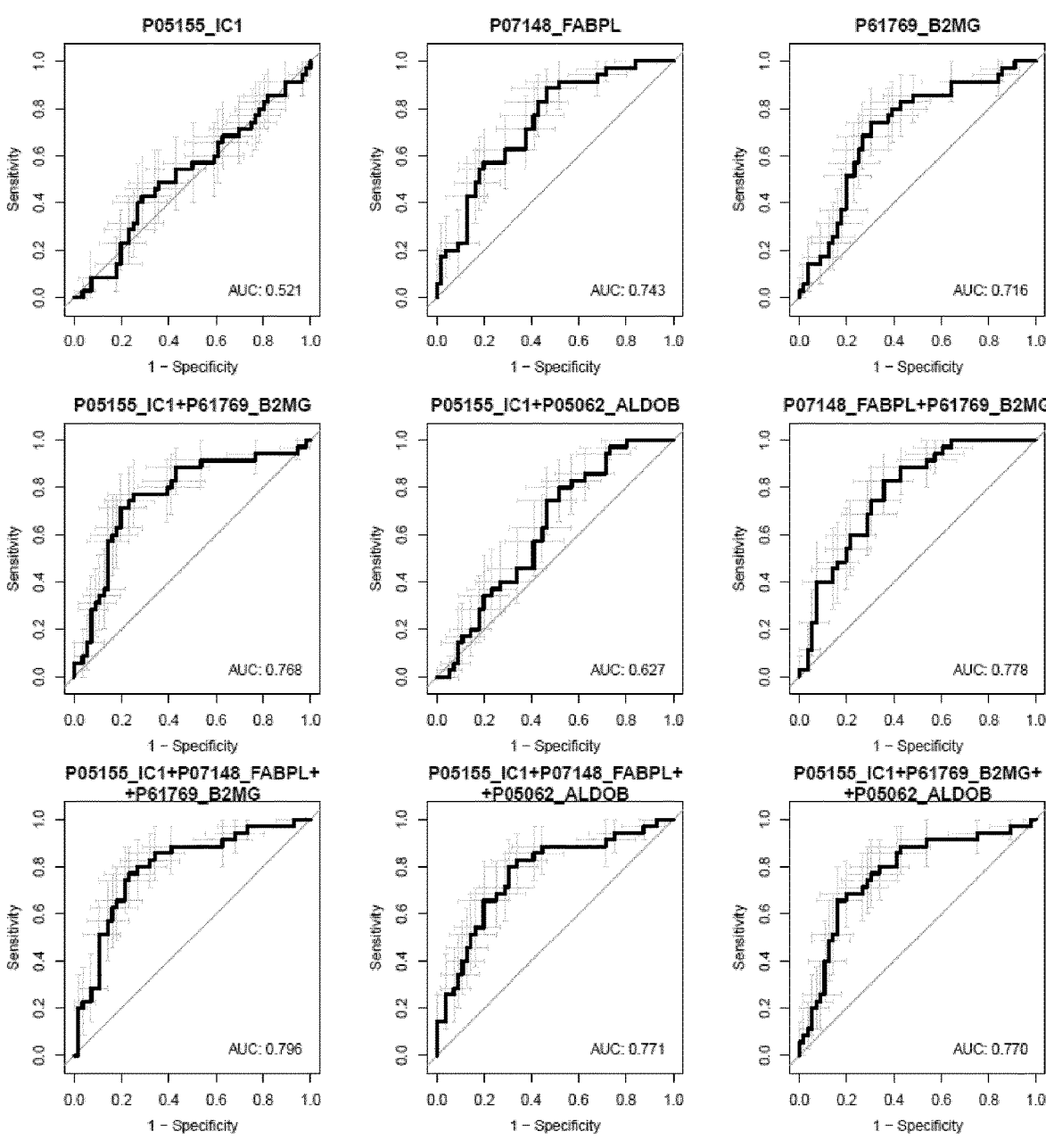
FIG. 8. ROC curves showing the AUC for the individual proteins L-FABP, B2MG, ALDOB and IC1, and combinations thereof, for predicting mortality risk among patients suffering from CS, when said proteins are not combined with CardShock and are measured by mass spectrometry.
Figure 8:
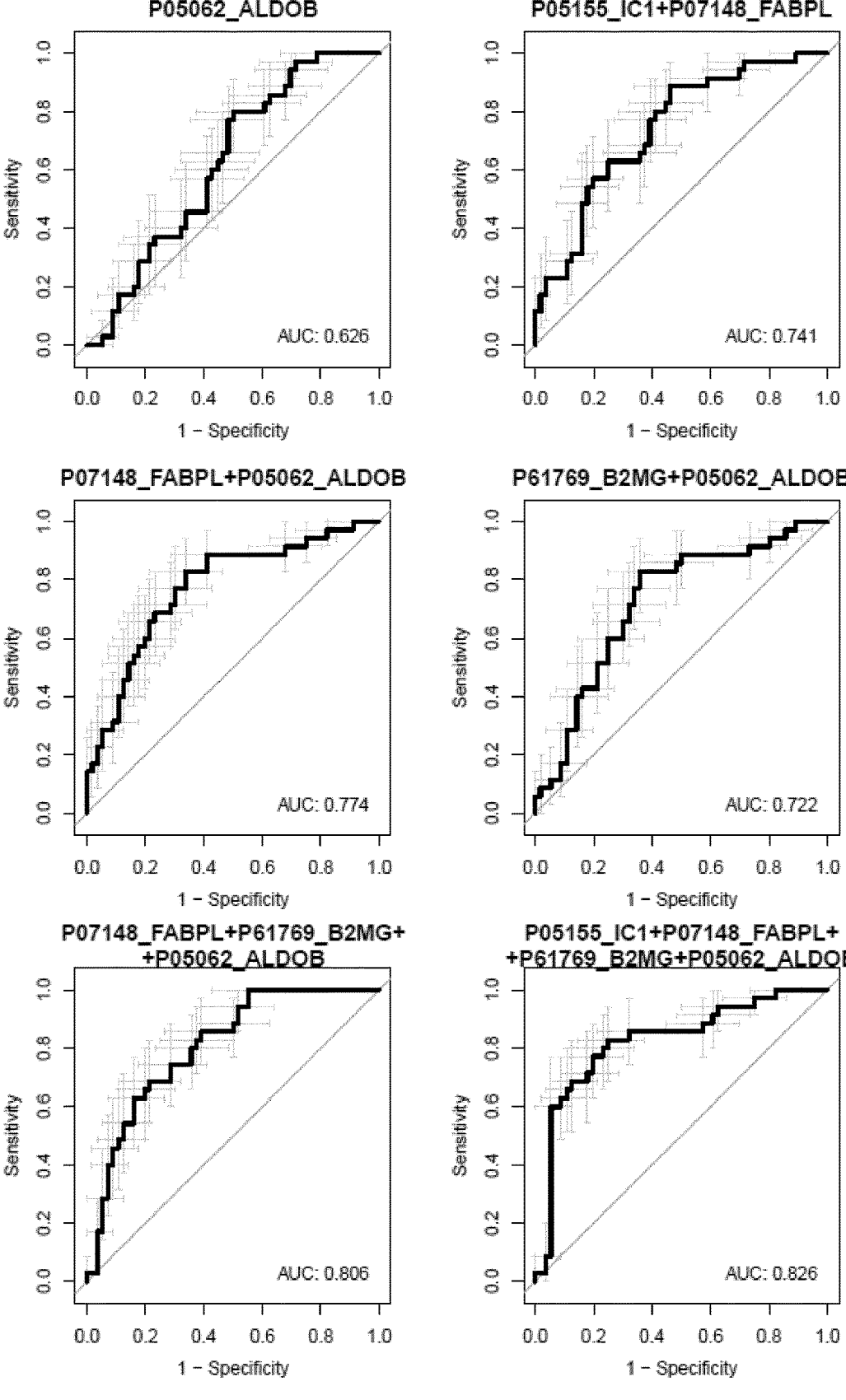
Figure 9:
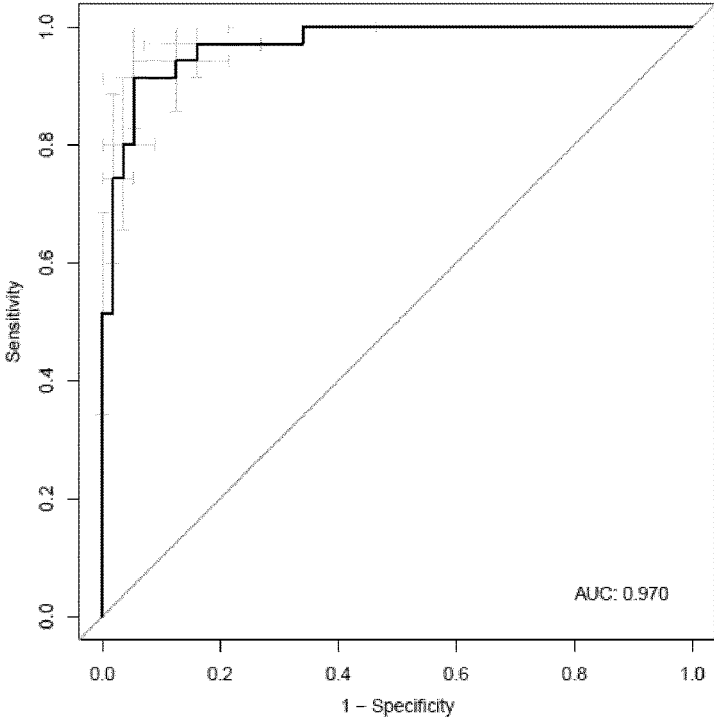
FIG. 9. ROC curves showing the AUC for a model based on the combination of the twenty-six proteins listed in Table 1, for predicting mortality risk among patients suffering from CS, when said proteins are combined with CardShock.
Figure 10:
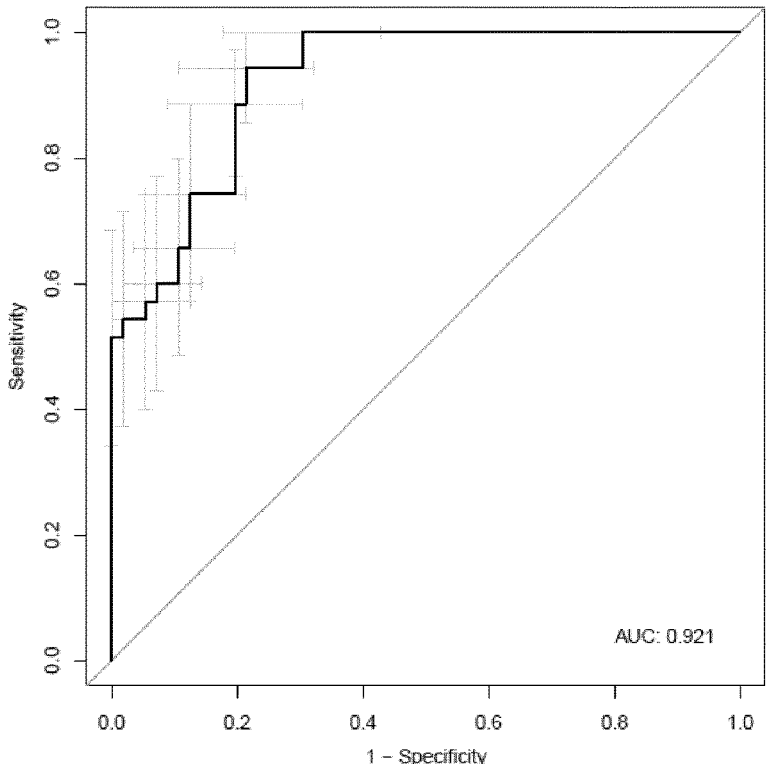
FIG. 10. ROC curves showing the AUC for a model based on the combination of the twenty-six proteins listed in Table 1, for predicting mortality risk among patients suffering from CS, when said proteins are not combined with Card-Shock.
Figure 11:
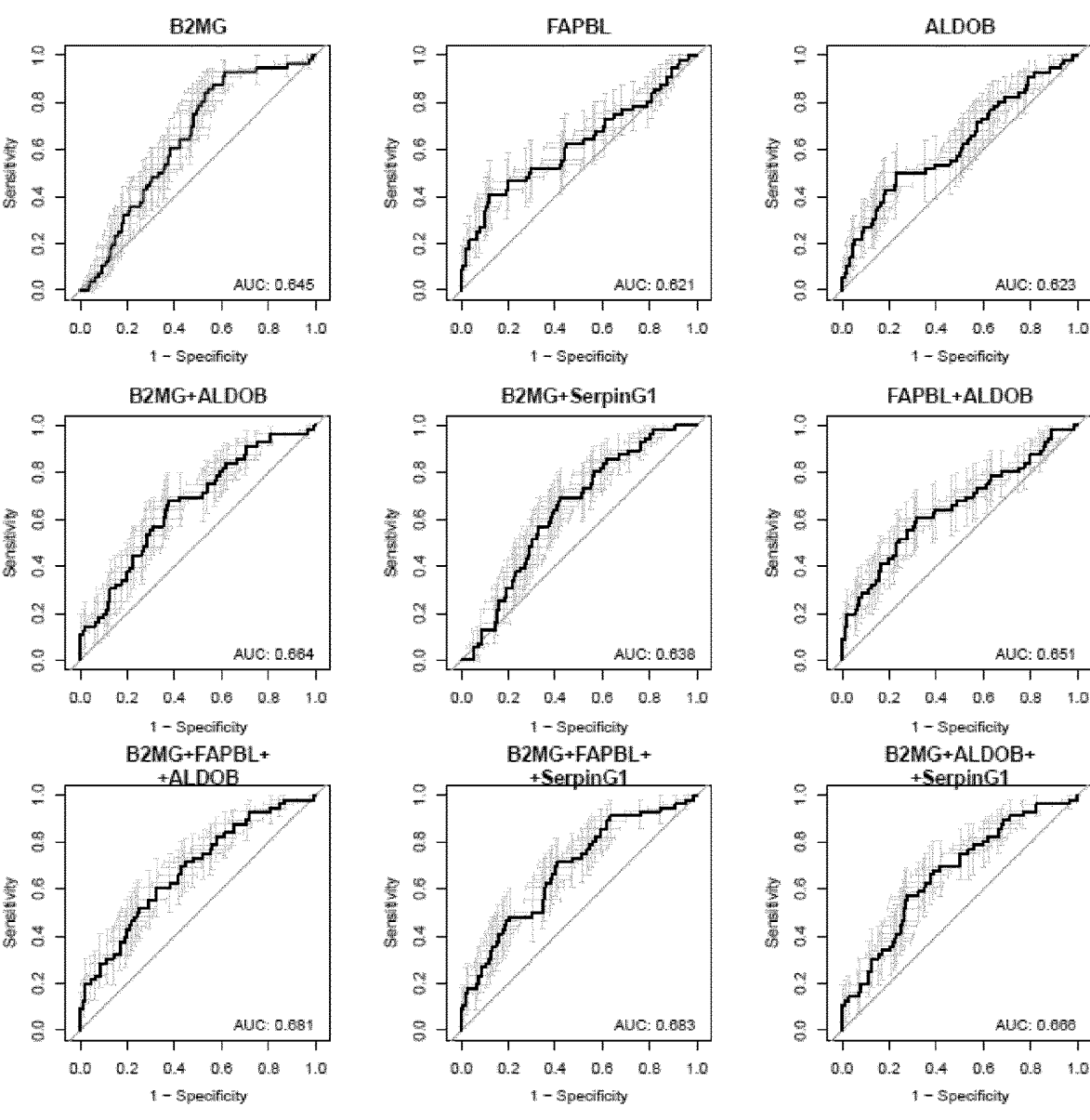
FIG. 11. ROC curves showing the AUC for the individual proteins L-FABP, B2MG, ALDOB and IC1 and combinations thereof, for predicting mortality risk among patients suffering from SS, within a period of 30 days. Experiments performed by ELISA.
Figure 11:
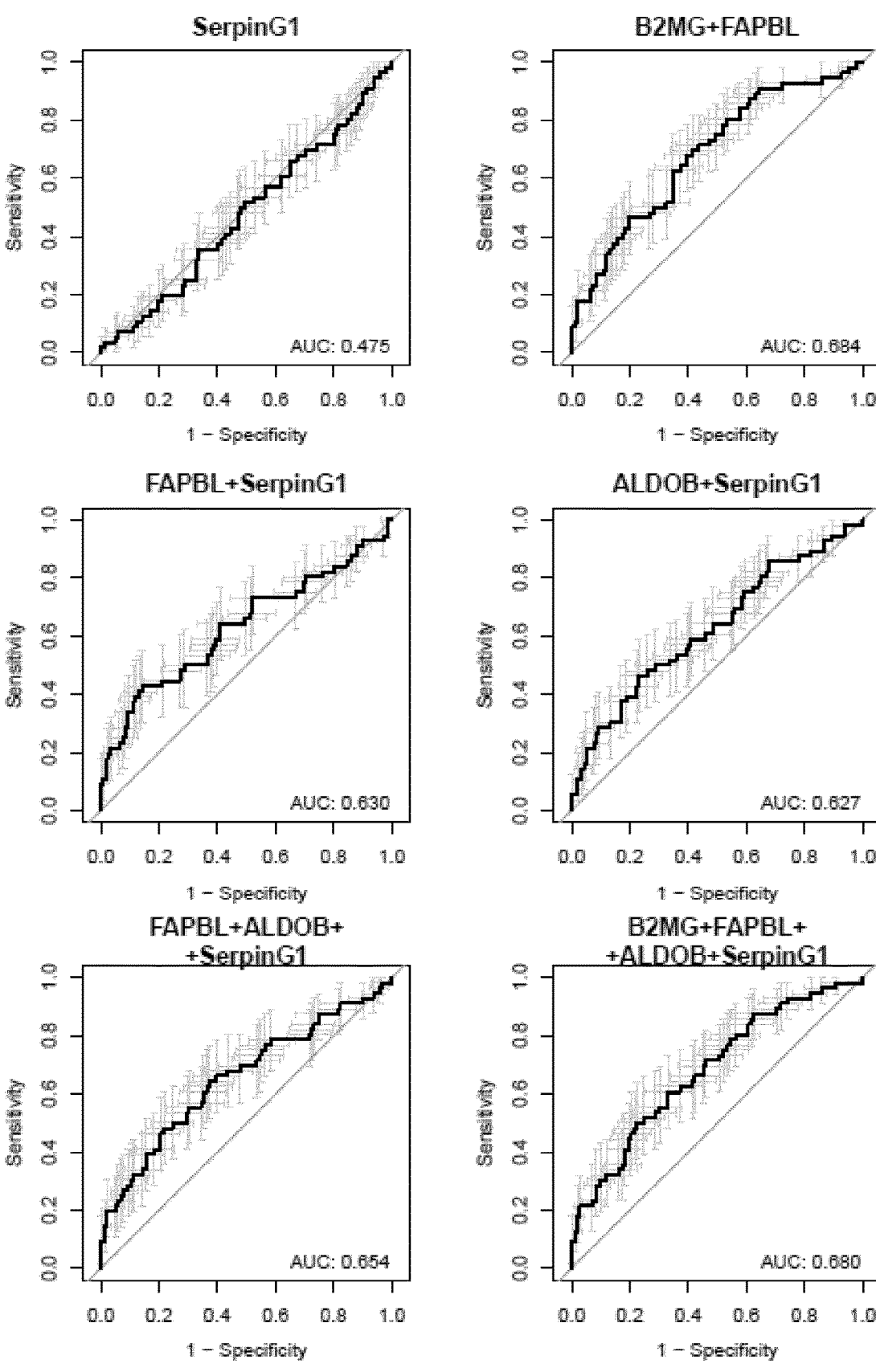
Figure 12:
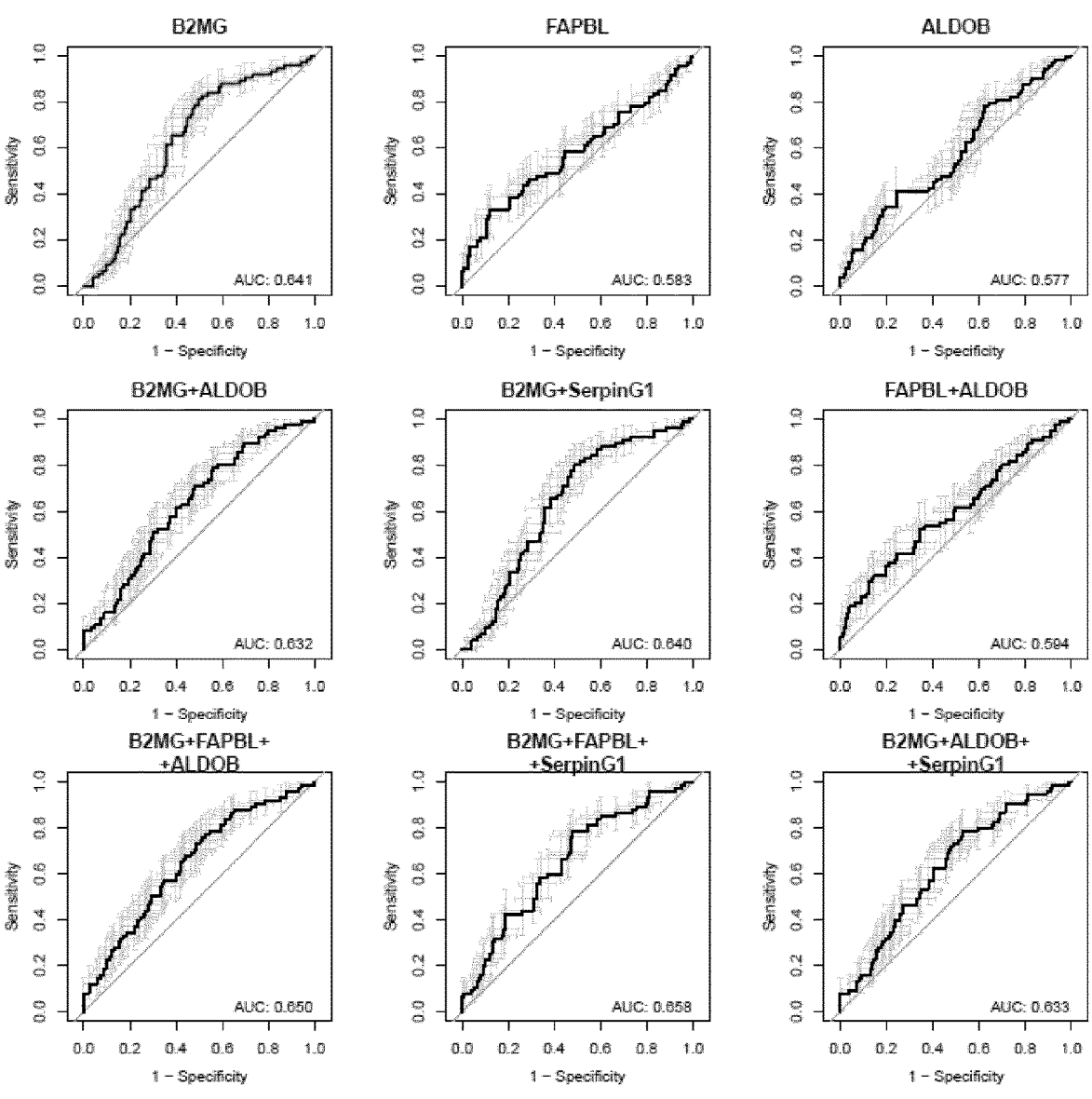
FIG. 12. ROC curves showing the AUC for the individual proteins L-FABP, B2MG, ALDOB and IC1 and combinations thereof, for predicting mortality risk among patients suffering from SS, within a period of 90 days. Experiments performed by ELISA.
Figure 12:
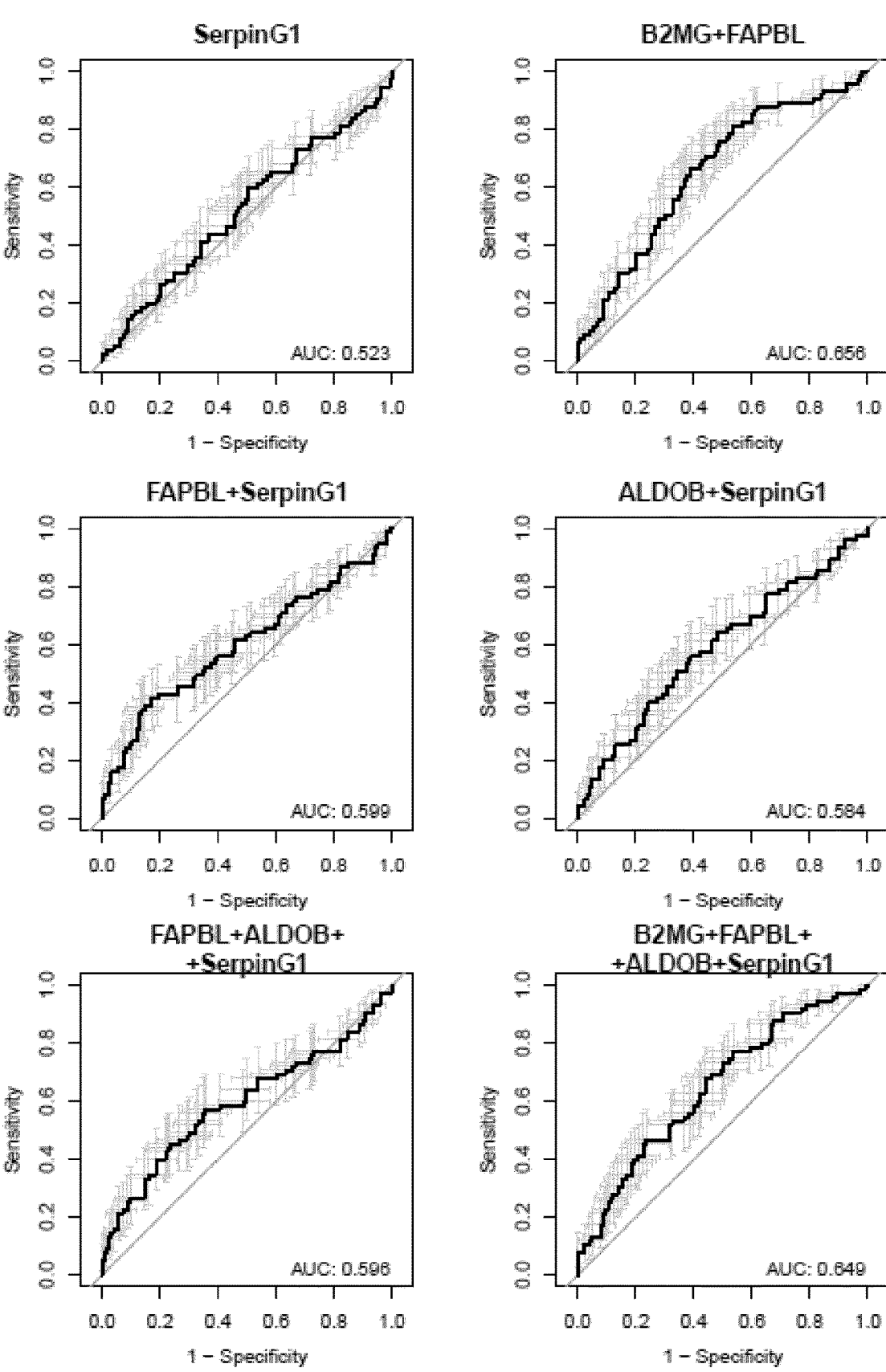
Figure 13:
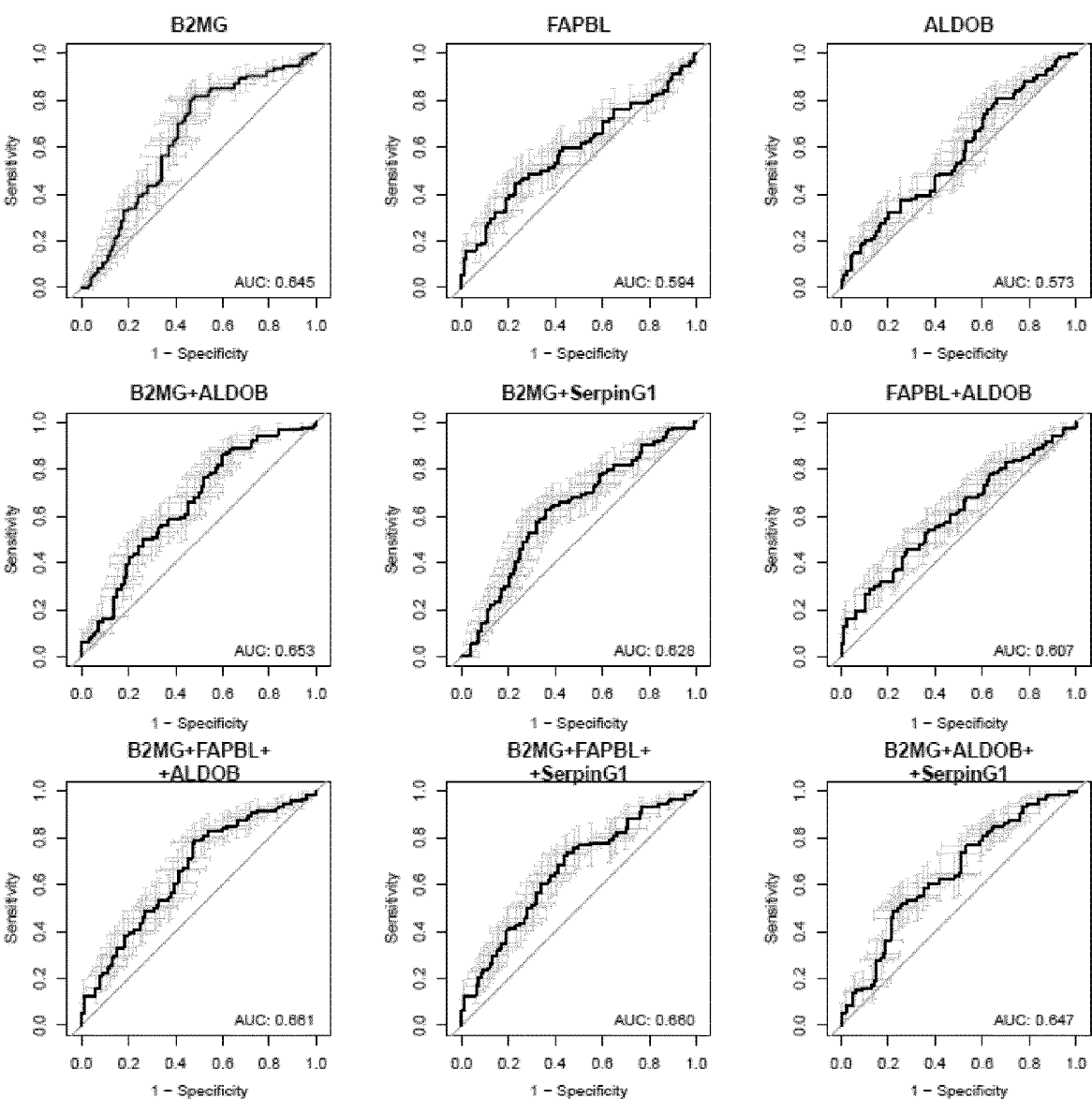
FIG. 13. ROC curves showing the AUC for the individual proteins L-FABP, B2MG, ALDOB and IC1 and combinations thereof, for predicting mortality risk among patients suffering from SS, within a period of 365 days. Experiments performed by ELISA.
Figure 13:
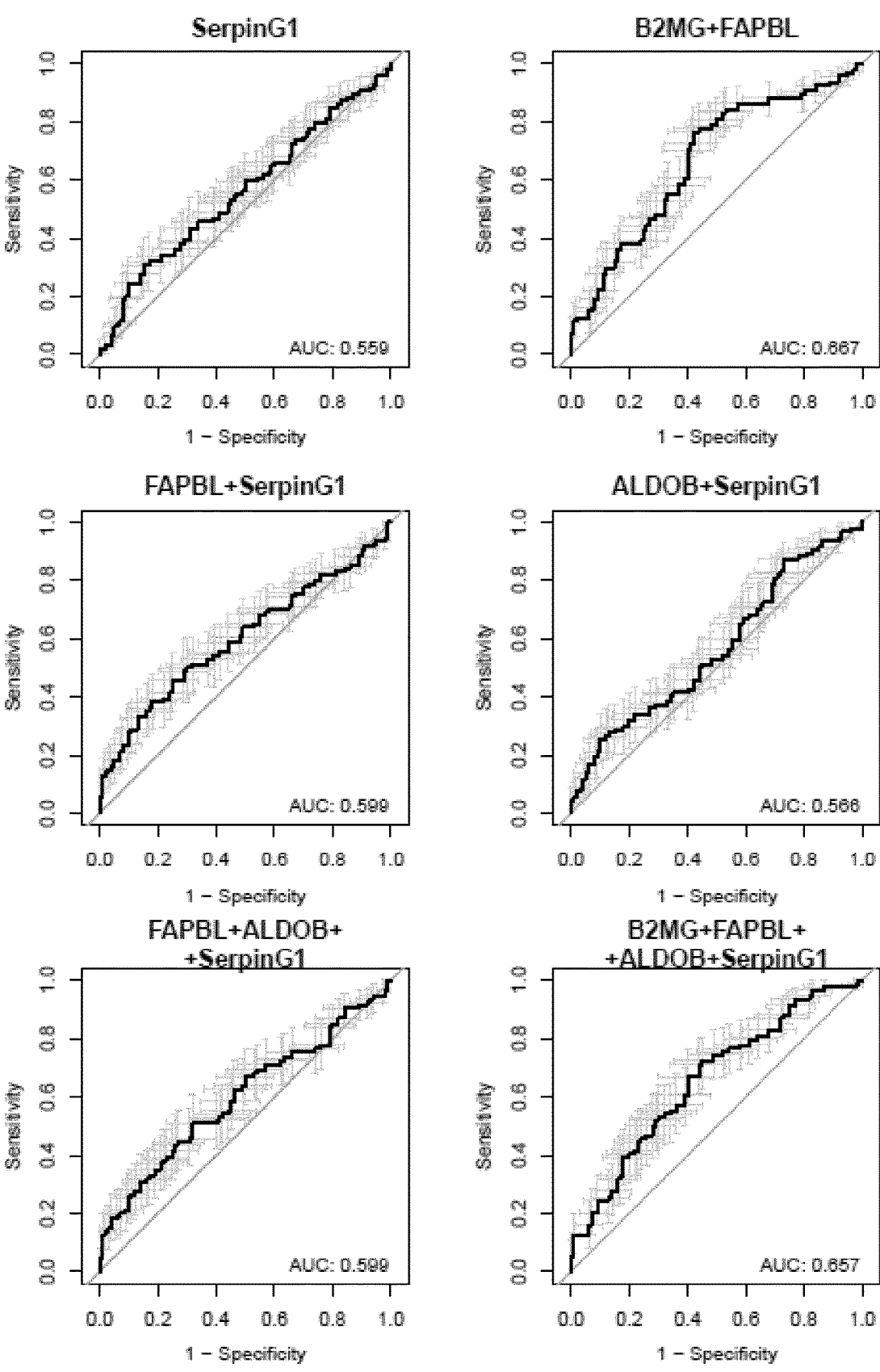

Example 2.3. Translation of CS4P into Enzyme-Linked Immunosorbent Assays (ELISA) in CS The CS4P model defined by targeted proteomics was tested by ELISA to support its prompt translation into routine clinical practice. Median (IQR) circulating concentrations of the studied proteins were: L-FABP, 160 pg/mL (42-1720 pg/mL); B2MG, 482 μg/mL (276-752 μg/mL); ALDOB, 101 ng/ml (70-209 ng/ml); and IC1, 218 pg/mL (169-259 pg/mL), respectively. Circulating L-FABP (453 vs. 94 pg/mL, p=0.02), B2MG (709 vs. 344 μg/mL, p<0.001), and ALDOB (156 vs. 84 ng/mL, p=0.05) were higher in non-survivors relative to survivors. By contrast, IC1 concentration was significantly lower in non-survivors relative to survivors (205 vs. 226 pg/mL, p=0.02) (FIG. 4).

Protein concentrations of the CS4P obtained by ELISA combined with the CardShock risk score provided an AUC of 0.82 (95% CI 0.73-0.90), not significantly different from that obtained by targeted proteomics (p=0.123).

Example 2.4. Translation of CS4P into Enzyme-Linked Immunosorbent Assays (ELISA) in SS The CS4P model defined by targeted proteomics was tested by ELISA to support its prompt translation into routine clinical practice. Median (IQR) circulating concentrations of the studied proteins were: L-FABP, 34.29 pg/mL (0.6-2500 pg/mL); B2MG, 1034 μg/mL (204-4637 μg/mL); ALDOB, 91.43 ng/ml (38-637 ng/ml); and IC1, 217 pg/mL (19-500 pg/mL), respectively. Circulating L-FABP (p=0.002, OR 1.47, 95% CI 1.18-1.44), B2MG (p<0.001, OR 1.42, 95% CI 1.14-1.77), and ALDOB (p=0.007, OR 1.34, 95% CI 1.08-1.65) were higher in non-survivors relative to survivors after analysing all-cause of death at 30 days in a univariate analysis. In the multivariable analysis, L-FABP (p=0.004, HR 1.38, 95% CI 1.10-1.69) and B2MG (p=0.001, HR 1.44, 95% CI 1.16-1.80) were higher in non-survivors relative to survivors after analysing all-cause of death at 30 days.

Protein concentrations of the CS4P obtained by ELISA provided an AUC of 0.68 (95% CI 0.60-0.76).

TABLES

TABLE 1

Twenty-six protein biomarkers used for patient classification.

| Protein Name | Uniprot Reference |
|---|---|
| B2MG (Beta-2-microglobulin) | P61769 |
| FABPL (Liver-fatty acid-binding protein) | P07148 |
| ALDOB (Fructose-bisphosphate aldolase B) | P05062 |
| IC1 (SerpinG1) | P05155 |
| F13A (Coagulation factor XIII A chain) | P00488 |
| HPTR (Haptoglobin-related protein) | P00739 |
| PLMN (Plasminogen) | P00747 |
| AACT (Alpha-1-antichymotrypsin) | P01011 |
| ANGT (Angiotensinogen) | P01019 |
| FIBA (Fibrinogen alpha chain) | P02671 |
| FIBB (Fibrinogen beta chain) | P02675 |
| FIBG (Fibrinogen gamma chain) | P02679 |
| CRP (C-reactive protein) | P02741 |
| RET4 (Retinol-binding protein 4) | P02753 |
| S10A8 (Protein S100-A8) | P05109 |
| HEP2 (Heparin cofactor 2) | P05546 |
| IBP2 (Insulin-like growth factor-binding protein 2) | P18065 |
| MUC18 (Cell surface glycoprotein MUC18) | P43121 |
| SEPP1 (Selenoprotein P) | P49908 |
| ILRL1 (Interleukin-1 receptor-like 1) | Q01638 |
| FHR4 (Complement factor H-related protein 4) | Q92496 |
| CELR1 (Cadherin EGF LAG seven-pass G-type receptor 1) | Q9NYQ6 |
| MYO5A (Unconventional myosin-Va) | Q9Y4I1 |
| CATA (Catalase) | P04040 |
| ALDOA (Fructose-bisphosphate aldolase A) | P04075 |
| APOB (Apolipoprotein B-100) | P04114 |

TABLE 2

Four proteins identified as reliable individual biomarkers for predicting mortality risk among patients suffering from CS (+CS: Combined with CardSock. −CS: Not combined with CardSock. E: ELISA technique. MS: Mass spectrometry technique).

| Protein Name | Uniprot Reference | AUC | | | |
|---|---|---|---|---|---|
| | | +CS E | +CS MS | −CS E | −CS MS |
| B2MG (Beta-2-microglobulin) | P61769 | 0.765 | 0.808 | 0.742 | 0.716 |
| FABPL (Liver-fatty acid-binding protein) | P07148 | 0.786 | 0.809 | 0.657 | 0.743 |

TABLE 2-continued

Four proteins identified as reliable individual biomarkers for predicting mortality risk among patients suffering from CS (+CS: Combined with CardSock. −CS: Not combined with CardSock. E: ELISA technique. MS: Mass spectrometry technique).

| Protein Name | Uniprot Reference | AUC | | | |
|---|---|---|---|---|---|
| | | +CS E | +CS MS | −CS E | −CS MS |
| ALDOB Fructose-bisphosphate aldolase B) | P05062 | 0.797 | 0.791 | 0.637 | 0.626 |
| IC1 (SerpinG1) | P05155 | 0.800 | 0.799 | 0.596 | 0.521 |

TABLE 3

Comparison of baseline characteristics, clinical presentation, management, analytical parameters, and outcome between the discovery and validation cohorts.

| Characteristic | Discovery cohort (n = 48) | Validation cohort (n = 97) | P value |
|---|---|---|---|
| Age, years | 69 (13) | 66 (14) | 0.204 |
| Women, n (%) | 17 (35) | 24 (25) | 0.179 |
| Medical history, n (%) | | | |
| Hypertension | 30 (62.5) | 57 (58.8) | 0.666 |
| Diabetes | 20 (41.7) | 29 (29.9) | 0.159 |
| Stroke/TIA | 6 (12.5) | 11 (11.3) | 0.838 |
| Heart failure | 5 (10.4) | 22 (22.7) | 0.074 |
| Coronary artery disease | 12 (25.0) | 34 (35.1) | 0.221 |
| Previous myocardial infarction | 4 (8.3) | 24 (24.7) | 0.018 |
| Prior PCI | 5 (10.4) | 16 (16.5) | 0.328 |
| Prior CABG | 1 (2.1) | 6 (6.2) | 0.278 |
| Clinical presentation | | | |
| Acute coronary syndrome, n (%) | 48 (100) | 69 (71.1) | <0.001 |
| STEMI, n (%) | 48 (100) | 50 (51.5) | <0.001 |
| Resuscitated from cardiac arrest, n (%) | 15 (31.3) | 20 (20.6) | 0.159 |
| Mean blood pressure, mmHg | 69 ± 20 | 57 ± 10 | <0.001 |
| Heart rate, bpm | 85 ± 29 | 92 ± 28 | 0.167 |
| LVEF, % | 39 ± 13 | 34 ± 15 | 0.057 |
| Management, n (%) | | | |
| Coronary angiography | 46 (95.8) | 73 (75.3) | 0.002 |
| PCI | 45 (93.8) | 58 (59.8) | <0.001 |
| TIMI flow after PCI | | | 0.104 |
| 0 | 0 (0) | 3 (5.1) | |
| 1 | 0 (0) | 4 (6.8) | |
| 2 | 4 (10.5) | 10 (16.9) | |
| 3 | 34 (89.5) | 42 (71.2) | |
| CABG | 0 (0) | 5 (5.3) | 0.104 |
| IABP | 27 (56.3) | 45 (46.4) | 0.264 |
| Biochemistry at admission | | | |
| Hemoglobin, g/L | 118 ± 24 | 128 ± 25 | 0.024 |
| Creatinine, mg/dL (IQR) | 1.6 (1.3-1.9) | 1.2 (0.9-1.6) | <0.001 |
| eGFR$_{CKD-EPI}$, mL/min/1.73 m$^2$ | 42 ± 15 | 63 ± 29 | <0.001 |
| Arterial blood lactate, mmol/L median (IQR) | 6.3 (4.6-15.0) | 2.5 (1.8-5.6) | 0.003 |
| Lactate >5 mmol/L, n (%) | 5 (71.4) | 26 (26.8) | 0.013 |
| Glucose, mmol/L | 16.9 ± 7.3 | 11.9 ± 6.0 | <0.001 |
| Glucose >10.6 mmol/L, n (%) | 38 (84.4) | 46 (48.4) | <0.001 |
| hsTnT, pg/mL, median (IQR) | 2116 (869-7690) | 1568 (277-3920) | 0.068 |
| NT-ProBNP, pg/mL, median (IQR) | 1945 (558-6984) | 3385 (687-9716) | 0.142 |
| 90-Day mortality, n (%) | 22 (45.8) | 36 (37.1) | 0.313 |

TIA denotes transient ischemic attack, PCI percutaneous coronary intervention, CABG coronary artery bypass grafting, STEMI ST-elevation myocardial infarction, LVEF left ventricular ejection fraction, TIMI thrombolysis in myocardial infarction, IABP intra-aortic balloon pump, $eGFR_{CKD\text{-}EPI}$ estimated glomerular filtration rate by the Chronic Kidney Disease Epidemiology Collaboration formula, hsTnT high-sensitivity troponin T, and NT-proBNP N-terminal pro-B-type natriuretic peptide.

TABLE 4

| | | | | | | |
|---|---|---|---|---|---|---|
| Comparison of model performances for predicting 90-day mortality in CS patients. | | | | | | |
| | AUC | P value | HL | P value | NRI | P value |
| CardShock | 0.78 (0.69-0.87) | — | 3.29 | 0.914 | — | — |
| CS4P | 0.83 (0.74-0.89) | 0.178* | 13.26 | 0.103 | — | — |
| CardShock + CS4P | 0.84 (0.76-0.93) | 0.033* | 7.250 | 0.509 | 0.49 | 0.020* |

*P values vs. CardShock. AUC denotes area under the curve, HL Hosmer-Lemeshow, and NRI net reclassification improvement. CardShock includes age>75 years, confusion at presentation, previous MI or CABG, ACS etiology, LVEF<40%, blood lactate, and $eGFR_{CKD\text{-}EPI}$. CS4P score includes liver-type fatty acid-binding protein (L-FABP), fructose-bisphosphate aldolase B (ALDOB), beta-2-microglobulin (B2MG), and SerpinG1 (IC1). CardShock+CS4P include CardShock plus CS4P score.

The invention claimed is:

1. A method of treating a human patient determined to have a mortality risk and who is suffering from cardiogenic shock, or who has suffered from cardiogenic shock, comprising:

treating the human patient having the mortality risk with a cardiogenic shock treatment, wherein the mortality risk has been determined by steps comprising:

a) obtaining a biological sample from the human patient, wherein the biological sample is a serum or plasma sample, or a combination thereof;

b) analyzing concentration levels of B2MG protein in a sample prepared from the biological sample, wherein the sample is analyzed by:

i) an enzyme-linked immunosorbent assay; or ii) a mass spectrometry assay;

c) comparing the concentration levels of the B2MG protein as analyzed in step b) relative to levels of B2MG protein in a biological sample from a control survivor human patient suffering from cardiogenic shock as analyzed by the same assay; and d) determining the mortality risk of the human patient, wherein an increased level of the B2MG with respect to the concentration level determined in the control survivor human patient suffering from cardiogenic shock is an indication of mortality risk.

2. The method of claim 1, wherein step b) further comprises analyzing concentration levels of L-FABP, and/or ALDOB and/or IC1 in the biological sample using the enzyme-linked immunosorbent assay or the mass spectrometry assay.

3. The method of claim 1, wherein step b) further comprises analyzing concentration levels of B2MG, L-FABP, ALDOB and IC1 in the biological sample using the enzyme-linked immunosorbent assay or the mass spectrometry assay.

4. The method of claim 1, wherein step b) further comprises analyzing concentration levels of FABPL, and/or ALDOB, and/or IC1, and/or F13A, and/or HPTR, and/or PLMN, and/or AACT, and/or ANGT, and/or FIBA, and/or FIBB, and/or FIBG, and/or CRP, and/or RET4, and/or S10A8, and/or HEP2, and/or IBP2, and/or MUC18, and/or SEPP1, and/or ILRL1, and/or FHR4, and/or CELR1, and/or MYO5A, and/or CATA, and/or ALDOA and/or APOB in the biological sample using the enzyme-linked immunosorbent assay or the mass spectrometry assay.

5. The method of claim 1, wherein the human patient is more than 75 years, has confusion at presentation, a previous myocardial infarction or coronary artery bypass grafting, acute coronary syndrome etiology and left ventricular ejection fraction of less than 40%, and the analytical method further comprises determining lactate and the estimated glomerular filtration rate (eGFRCKD-EPI).

6. The method of claim 1, wherein the method is performed within 24 hours from an admission of the human patient to a hospital.

7. The method of claim 1, wherein the method is performed within 90 days from an admission of the human patient to a hospital.

8. A method of treating a human patient having a mortality risk and who is suffering from cardiogenic shock, or has suffered from cardiogenic shock, comprising:

treating the human patient having the mortality risk with a cardiogenic shock treatment, wherein the cardiogenic shock treatment comprises treatment with a ventricular assist device, revascularization, hemodynamic stabilization, treatment of multiorgan system dysfunction, administration of anti-arrhythmic agents, administration of synchronized cardioversion, administration of positive inotropic agents, administration of mechanical circulatory support, treatment using extracorporeal life support systems, heart transplantation, or any combination thereof;

and wherein the mortality risk has been determined by steps comprising:

a) obtaining a biological sample from the human patient, wherein the biological sample is a serum or plasma sample, or a combination thereof;

b) analyzing concentration levels of B2MG protein in the biological sample by: i) an enzyme-linked immunosorbent assay; or ii) a mass spectrometry assay;

c) comparing the concentration levels of the B2MG protein as analyzed in step b) relative to levels of B2MG protein in a biological sample from a control survivor human patient suffering from cardiogenic shock as analyzed by the same assay; and d) determining the mortality risk, wherein an increased level of the B2MG with respect to the concentration level determined in the control survivor human patient suffering from cardiogenic shock is an indication of mortality risk.

9. The method of claim 8, wherein step b) further comprises determining the concentration level of the protein L-FABP, and/or ALDOB and/or IC1 in the biological sample obtained from the human patient, and step c) further comprises determining that a concentration level of the protein L-FABP or ALDOB is higher than the concentration a level of L-FABP or ALDOB in the control survivor human patient biological sample, and/or determining a level of the protein IC1 is lower than a concentration level of the protein IC1 in the control survivor human patient biological sample.

10. The method of claim 8, wherein step b) further comprises determining a concentration level of the proteins B2MG, L-FABP, ALDOB and IC1 in the biological sample obtained from the human patient, and step c) further comprises determining an increased level of the proteins B2MG, L-FABP and ALDOB relative to a level of B2MG, L-FABP and ALDOB, respectively, in the control survivor human patient biological sample, and further determining a decreased level of the protein IC1 relative to a level of IC1 in the control survivor human patient biological sample.

11. The method of claim 8, wherein step b) further comprises determining the concentration level of the proteins: FABPL, and/or ALDOB, and/or IC1, and/or F13A, and/or HPTR, and/or PLMN, and/or AACT, and/or ANGT, and/or FIBA, and/or FIBB, and/or FIBG, and/or CRP, and/or RET4, and/or S10A8, and/or HEP2, and/or IBP2, and/or MUC18, and/or SEPP1, and/or ILRL1, and/or FHR4, and/or CELR1, and/or MYO5A, and/or CATA, and/or ALDOA and/or APOB in the biological sample from the human patient.

12. The method of claim 8, wherein the human patient is more than 75 years, has confusion at presentation, a previous myocardial infarction or coronary artery bypass grafting, acute coronary syndrome etiology and left ventricular ejection fraction of less than 40%, and the analytical method further comprises determining lactate and the estimated glomerular filtration rate (eGFRCKD-EPI).

13. The method of claim 8, wherein the method is performed within 24 hours from an admission of the human patient to a hospital.

14. The method of claim 8, wherein the method is performed within 90 days from an admission of the human patient to a hospital.

15. The method of claim 8, wherein the determination of the concentration level of the B2MG protein is performed by ELISA, or by mass spectrometry.

* * * * *